United States Patent [19]

Shetty

[11] 4,085,107

[45] Apr. 18, 1978

[54] 1-HETEROCYCLIC ALKYL-1,2,3,4-TETRAHYDROQUINAZOLINONES

[75] Inventor: Bola Vithal Shetty, Rockville, Md.

[73] Assignee: Pennwalt Corporation, Philadelphia, Pa.

[21] Appl. No.: 716,856

[22] Filed: Aug. 23, 1976

Related U.S. Application Data

[60] Continuation-in-part of Ser. No. 452,587, Mar. 19, 1974, abandoned, which is a continuation of Ser. No. 108,659, Jan. 21, 1971, abandoned, which is a division of Ser. No. 691,955, Dec. 20, 1967, Pat. No. 3,635,976.

[51] Int. Cl.$^2$ ............................................. C07D 239/88
[52] U.S. Cl. .............................. 260/256.4 Q; 424/251
[58] Field of Search ................................. 260/256.4 Q

[56] References Cited

U.S. PATENT DOCUMENTS 3,497,514  2/1970  Okumura et al. .................... 424/251

Primary Examiner—Paul M. Coughlan, Jr.
Attorney, Agent, or Firm—William D. Mitchell

[57] ABSTRACT

1-Heterocyclic alkyl-1,2,3,4-tetrahydroquinazolinones, acid addition salts thereof, and intermediate compounds having analgesic properties. A representative quinazolinone compound is 1-[2-(1-phenyl-4-piperazinyl)-ethyl]-2-phenyl-1,2,3,4-tetrahydro-4-quinazolinone. A representative analgesic intermediate is 2-[2-(4-[1-phenyl]-piperazinyl) ethylamino] benzamide.

5 Claims, No Drawings

# 1-HETEROCYCLIC ALKYL-1,2,3,4-TETRAHYDROQUINAZOLINONES

CROSS REFERENCES

This application is a continuation-in-part of Application Ser. No. 452,587, filed Mar. 19, 1974 abandoned, which in turn is a continuation of Application Ser. No. 108,659, filed Jan. 21, 1971 (now abandoned), which in turn is a division of Application Ser. No. 691,955 filed Dec. 20, 1967 (now U.S. Pat. No. 3,635,976).

The invention relates to 1-heterocyclic alkyl-1,2,3,4-tetrahydroquinazolinones, acid addition salts, and intermediate compounds thereof characterized by having analgesic properties.

More particularly the invention relates to compounds from the group consisting of A, compounds of the formula:

wherein
X is NH, $NR_1$, $CH_2$, $CHR_1$, $$C\begin{matrix}R_1\\R_6\end{matrix},$$

O or S; $R_6$ is OH or $OCOR_7$ wherein $R_7$ is loweralkyl, e.g., $CH_3$, $CH_2$—$CH_3$, $CH_2CH_2CH_3$ or $$CH\begin{matrix}CH_3\\CH_3\end{matrix};$$

A is $(CH_2)_n$ where $n$ is 1–5, or a branched alkylene with 3 to 5 carbon atoms;

R is H, loweralkyl, hydroxy, loweralkoxy, halogen, amino, or substituted amino (e.g.—$NHCOCH_3$, —NHCHO), $NO_2$;

$R_1$ is H, loweralkyl, aryl, or substituted aryl (e.g. $NH_2$, OH, $OCH_3$, $CH_3$, Cl)

$R_2$ is H, loweralkyl $R_3$ and $R_4$ each is H, aryl, substituted aryl (e.g. $NH_2$, $CH_3CONH$—, OH, $OCH_3$, $CH_3$, Cl), aralkyl, substituted aralkyl (e.g. OH, $NH_2$, $OCH_3$, $CH_3$, Cl), loweralkyl, or heterocyclic, $R_3$ and $R_4$ can be joined together to form with the two position carbon atom to which they are attached, a cycloaliphatic or heterocyclic ring substituted or unsubstituted preferably having 3 to 10 carbon atoms, $R_5$ is H, loweralkyl, aryl, substituted aryl, or aralkyl; "aryl" as used herein preferably being phenyl and "lower alkyl" preferably having 1–4 carbons; B, compounds of the formula:

wherein
X is NH, $NR_1$, $CH_2$, $CHR_1$, $$C\begin{matrix}R_1\\R_8\end{matrix},$$

where $R_8$ is OH or $OOR_9$, and $R_9$ is loweralkyl; or O or S,

R is H, loweralkyl, hydroxy, loweralkoxy, halogen, amino, or substituted amino group (e.g. NHCHO, NH—$CH_3$), $NO_2$;

A is $(CH_2)_n$ where $n$ is 1–5, or a branched alkylene with 3 to 5 carbon atoms, $R_1$ is H, loweralkyl, aryl, substituted aryl (e.g. OH, $OCH_3$, $NH_2$, $CH_3$, Cl), aralkyl, or substituted aralkyl (e.g. OH, $OCH_3$, $NH_2$, $CH_3$, Cl), $R_2$ is H, loweralkyl, $R_6$ is H, loweralkyl, alkanoyl, benzoyl, aryl, substituted aryl, aralkyl, substituted aralkyl, benzyl, substituted benzyl (e.g. OH, $OCH_3$, $NH_2$, $CH_3$, Cl), or heterocyclic.

$R_7$ is OH, loweralkoxy, (e.g. $OCH_3$, $OCH_3CH_3$), heterocyclic (e.g. —N⟨S⟩, —N⟨ ⟩, —N⟨O⟩, —N⟨N—$CH_3$⟩, —N⟨N—phenyl⟩, )

$NH_2$, —NH— loweralkyl, or —N=(disubstituted with loweralkyl), and C pharmacologically acceptable acid addition salts of the above compounds of A and B.

The compounds of the present invention may be prepared by various methods which are known in principle. A convenient method is illustrated in the following diagram of a general synthetic route, wherein R, R' and R" represent radicals such as shown in the formulae above. There are also given below two synthetic schemes for the preparation of specific compounds of this invention. The schematic and short hand representations are those known in the art.

GENERAL SYNTHETIC ROUTE
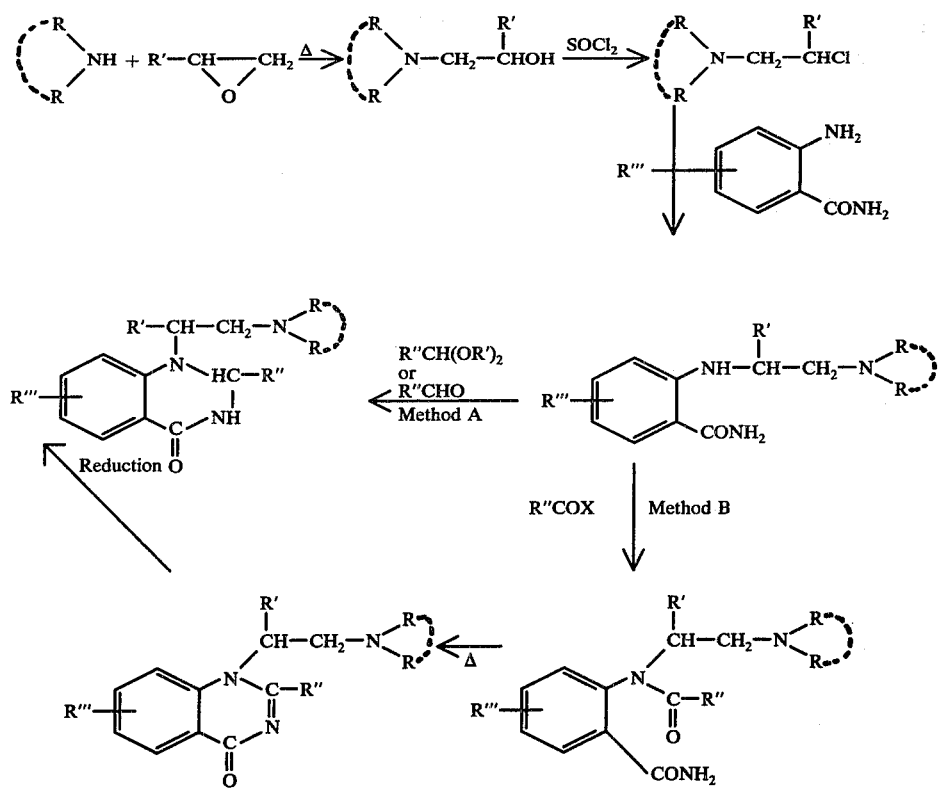
Synthetic Scheme for the Preparation of
2-[2-(4-[1-Phenyl]piperazinyl)ethylamino]-benzamide and
1-[2-(1-Phenyl-4-piperazinyl) ethyl]-2-phenyl-1,2,3,4-tetrahydro-4-quinazolinone
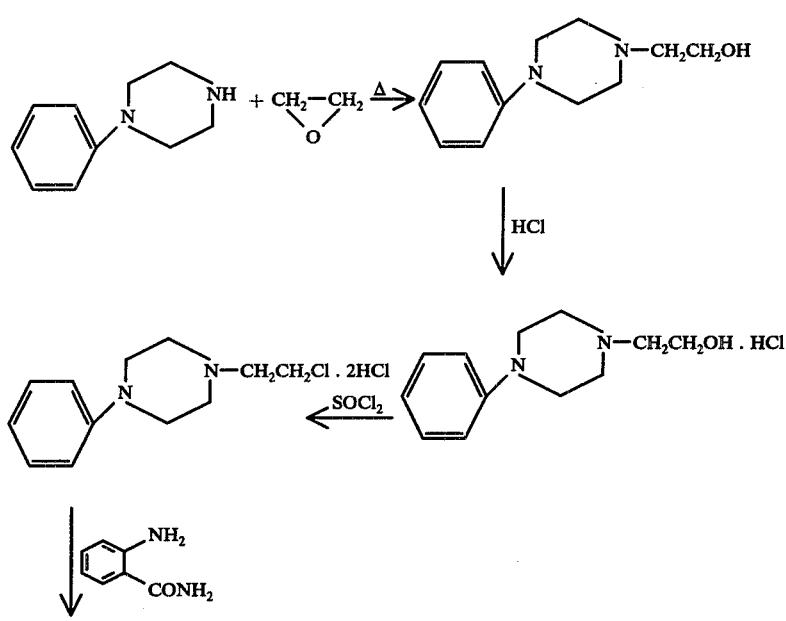

-continued
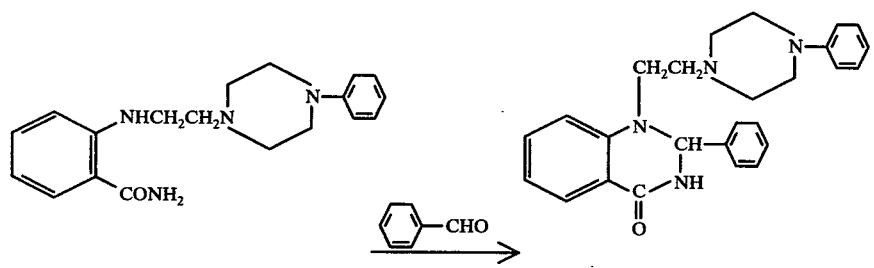
Alternate Route for the Synthesis of 1-[2-(1-Phenyl-4-piperazinyl)-ethyl]-
2-phenyl-1,2,3,4-tetrahydro-4-quinazolinone
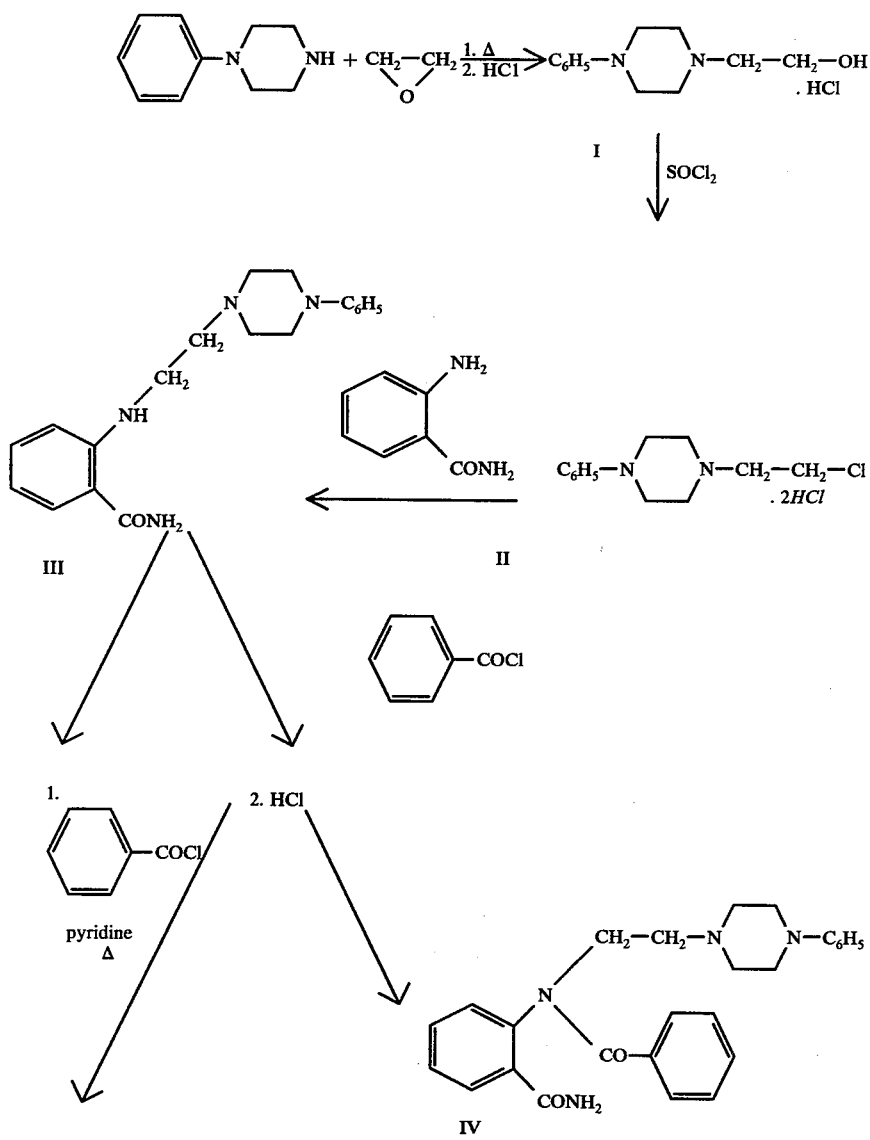

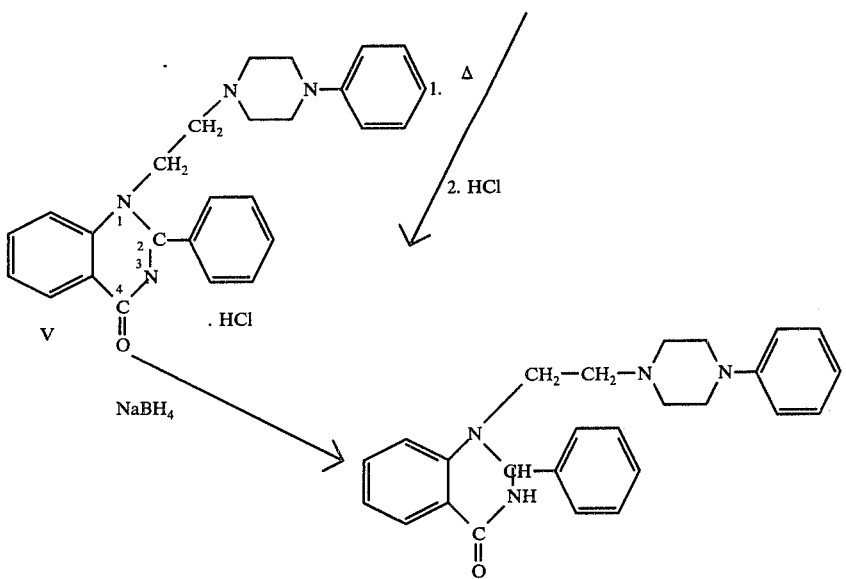

Typical examples of 1-piperazinyl-1,2,3,4-tetrahydro-4-quinazolinones which are effective analgesics for warm blooded animals are as follows:

2-(o-Aminophenyl)-1-[2-(1-Phenyl-4-piperazinyl)-ethyl]-1,2,3,4-tetrahydro-4-quinazolinone
2-(m-Aminophenyl)-1-[2-(1-Phenyl-4-piperazinyl)-ethyl]-1,2,3,4-tetrahydro-4-quinazolinone
2-(p-Aminophenyl)-1-[2-(1-Phenyl-4-piperazinyl)-ethyl]-1,2,3,4-tetrahydro-4-quinazolinone
2-(o-Methoxyphenyl)-1-[2-(1-Phenyl-4-piperazinyl)-ethyl]-1,2,3,4-tetrahydro-4-quinazolinone
2-(m-Methoxyphenyl)-1-[2-(1-Phenyl-4-piperazinyl)-ethyl]-1,2,3,4-tetrahydro-4-quinazolinone
2-(p-Methoxyphenyl)-1-[2-(1-Phenyl-4-piperazinyl)-ethyl]-1,2,3,4-tetrahydro-4-quinazolinone
2-(o-Hydroxyphenyl)-1-[2-(1-Phenyl-4-piperazinyl)-ethyl]-1,2,3,4-tetrahydro-4-quinazolinone
2-(m-Hydroxyphenyl)-1-[2-(1-Phenyl-4-piperazinyl)-ethyl]-1,2,3,4-tetrahydro-4-quinazolinone
2-(p-Hydroxyphenyl)-1-[2-(1-Phenyl-4-piperazinyl)-ethyl]-1,2,3,4-tetrahydro-4-quinazolinone
2-(o-Chlorophenyl)-1-[2-(1-Phenyl-4-piperazinyl)-ethyl]-1,2,3,4-tetrahydro-4-quinazolinone
2-(m-Chlorophenyl)-1-[2-(1-Phenyl-4-piperazinyl)-ethyl]-1,2,3,4-tetrahydro-4-quinazolinone
2-(p-Chlorophenyl)-1-[2-(1-Phenyl-4-piperazinyl)-ethyl]-1,2,3,4-tetrahydro-4-quinazolinone
2-(o-Bromophenyl)-1-[2-(1-Phenyl-4-piperazinyl)-ethyl]-1,2,3,4-tetrahydro-4-quinazolinone
2-(m-Bromophenyl)-1-[2-(1-Phenyl-4-piperazinyl)-ethyl]-1,2,3,4-tetrahydro-4-quinaqolinone
2-(p-Bromophenyl)-1-[2-(1-Phenyl-4-piperazinyl)-ethyl]-1,2,3,4-tetrahydro-4-quinazolinone
1-[2-(1-Phenyl-4-piperazinyl)-ethyl]-2-(o-tolyl)-1,2,3,4-tetrahydro-4-quinazolinone
1-[2-(1-Phenyl-4-piperazinyl)-ethyl]-2-(m-tolyl)-1,2,3,4-tetrahydro-4-quinazolinone
1-[2-(1-Phenyl-4-piperazinyl)-ethyl]-2-(p-tolyl)-1,2,3,4-tetrahydro-4-quinazolinone
2-Cyclohexyl-1-[2-(1-phenyl-4-piperazinyl)-ethyl]-1,2,3,4-tetrahydro-4-quinazolinone
2-(o-Carboxyphenyl)-1-[2-(1-phenyl-4-piperazinyl)-ethyl]-1,2,3,4-tetrahydro-4-quinazolinone
2-(m-Carboxyphenyl)-1-[2-(1-phenyl-4-piperazinyl)-ethyl]-1,2,3,4-tetrahydro-4-quinazolinone
2-(p-Carboxyphenyl)-1-[2-(1-phenyl-4-piperazinyl)-ethyl]-1,2,3,4-tetrahydro-4-quinazolinone
2-(o-Carbomethoxyphenyl)-1-[2-(1-phenyl-4-piperazinyl)-ethyl]-1,2,3,4-tetrahydro-4-quinazolinone
2-(m-Carbomethoxyphenyl)-1-[2-(1-phenyl-4-piperazinyl)-ethyl]-1,2,3,4-tetrahydro-4-quinazolinone
2-(p-Carbomethoxyphenyl)-1-[2-(1-phenyl-4-piperazinyl)-ethyl]-1,2,3,4-tetrahydro-4-quinazolinone
1-[2-(1-Phenyl-4-piperazinyl)-ethyl]-2-(2-pyridyl)-1,2,3,4-tetrahydro-4-quinazolinone
1-[2-(1-Phenyl-4-piperazinyl)-ethyl]-2-(3-pyridyl)-1,2,3,4-tetrahydro-4-quinazolinone
1-[2-(1-Phenyl-4-piperazinyl)-ethyl]-2-(4pyridyl)-1,2,3,4-tetrahydro-4-quinazolinone
1-[2-(1-Phenyl-4-piperazinyl)-ethyl]-2-(2-pyridylmethyl)-1,2,3,4-tetrahydro-4-quinazolinone
1-[2-(1-Phenyl-4-piperazinyl)-ethyl]-2-(3-pyridylmethyl)-1,2,3,4-tetrahydro-4-quinazolinone
1-[2-(1-Phenyl-4-piperazinyl)-ethyl]-2-(4-pyridylmethyl)-1,2,3,4-tetrahydro-4-quinazolinone
2-Morpholinyl-1-[2-(1-phenyl-4-piperazinyl)-ethyl]-1,2,3,4-tetrahydro-4-quinazolinone
2-Benzyl-1-[2-(1-phenyl-4-piperazinyl)-ethyl]-1,2,3,4-tetrahydro-4-quinazolinone
2-(o-Aminobenzyl)-1-[2-(1-phenyl-4-piperazinyl)-ethyl]-1,2,3,4-tetrahydro-4-quinazolinone
2-(m-Aminobenzyl)-1-[2-(1-phenyl-4-piperazinyl)-ethyl]-1,2,3,4-tetrahydro-4-quinazolinone
2-(p-Aminobenzyl)-1-[2-(1-phenyl-4-piperazinyl)-ethyl]-1,2,3,4-tetrahydro-4-quinazolinone
2-(o-Methoxybenzyl)-1-[2-(1-phenyl-4-piperazinyl)-ethyl]-1,2,3,4-tetrahydro-4-quinazolinone
2-(m-Methoxybenzyl)-1-[2-(1-phenyl-4-piperazinyl)-ethyl]-1,2,3,4-tetrahydro-4-quinazolinone
2-(p-Methoxybenzyl)-1-[2-(1-phenyl-4-piperazinyl)-ethyl]-1,2,3,4-tetrahydro-4-quinazolinone 2-(o-Hydroxybenzyl)-1-[2-(1-phenyl-4-piperazinyl)-ethyl]-1,2,3,4-tetrahydro-4-quinazolinone
2-(m-Hydroxybenzyl)-1-[2-(1-phenyl-4-piperazinyl)-ethyl]-1,2,3,4-tetrahydro-4-quinazolinone
2-(p-Hydroxybenzyl)-1-[2-(1-phenyl-4-piperazinyl)-ethyl]-1,2,3,4-tetrahydro-4-quinazolinone
1-[2-(1-phenyl-4-piperazinyl)-ethyl]-1,2,3,4-tetrahydro-4-quinazolinone
2-Methyl-1-[2-(1-phenyl-4-piperazinyl)-ethyl]-1,2,3,4-tetrahydro-4-quinazolinone
2-Ethyl-1-[2-(1-phenyl-4-piperazinyl)-ethyl]-1,2,3,4-tetrahydro-4-quinazolinone
1-[2-(1-phenyl-4-piperazinyl)-ethyl]-2-propyl-1,2,3,4-tetrahydro-4-quinazolinone
2,2-Dimethyl-1-[2-(1-phenyl-4-piperazinyl)-ethyl]-1,2,3,4-tetrahydro-4-quinazolinone
1'-[2-(1-phenyl-4-piperazinyl)-ethyl]spiro(cyclopentane-1,2'(1'H)-quinazolin)-4'(3'H)-one
1'-[2-(1-phenyl-4-piperazinyl)-ethyl]spiro(cyclohexane-1,2'(1'H)-quinazolin)-4'(3'H)-one
1-Methyl-1'-[2-(1-phenyl-4-piperazinyl)-ethyl]spiro[piperidine-4,2'(1'H)-quinazolin]-4'(3'H)-one
5-Amino-2-phenyl-1-[2-(1-phenyl-4-piperazinyl)-ethyl]-1,2,3,4-tetrahydro-4-quinazolinone
6-Amino-2-phenyl-1-[2-(1-phenyl-4piperazinyl)-ethyl]-1,2,3,4-tetrahydro-4-quinazolinone
7-Amino-2-phenyl-1-[2-(1-phenyl-4-piperazinyl)-ethyl]-1,2,3,4-tetrahydro 4-quinazolinone
8-Amino-2-phenyl-1-[2-(1-phenyl-4-piperazinyl)-ethyl]-1,2,3,4-tetrahydro-4-quinazolinone
5-Methoxy-2-phenyl-1-[2-(1-phenyl-4-piperazinyl)-ethyl]-1,2,3,4-tetrahydro-4-quinazolinone
6-Methoxy-2-phenyl-1-[2-(1-phenyl-4-piperazinyl)-ethyl]-1,2,3,4-tetrahydro-4-quinazolinone
7-Methoxy-2-phenyl-1-[2-(1-phenyl-4-piperazinyl)-ethyl]-1,2,3,4-tetrahydro-4-quinazolinone
8-Methoxy-2-phenyl-1-[2-(1-phenyl-4-piperazinyl)-ethyl]-1,2,3,4tetrahydro-4-quinazolinone
5-Hydroxy-2-phenyl-1-[2-(1-phenyl-4-piperazinyl)-ethyl]-1,2,3,4-tetrahydro-4-quinazolinone
6-Hydroxy-2-phenyl-1-[2-(1-phenyl-4piperazinyl)-ethyl]-1,2,3,4-tetrahydro-4-quinazolinone
7-Hydroxy-2-phenyl-1-[2-(1-phenyl-4-piperazinyl)-ethyl]-1,2,3,4-tetrahydro-4-quinazolinone
8-Hydroxy-2-phenyl-1-[2-(1-phenyl-4 -piperazinyl)-ethyl]1,2,3,4-tetrahydro-4-quinazolinone
5-Chloro-2-phenyl-1-[2-(1-phenyl-4-piperazinyl)-ethyl]-1,2,3,4-tetrahydro-4-quinazolinone
6-Chloro-2-phenyl-1-[2-(1-phenyl-4-piperazinyl)-ethyl]-1,2,3,4-tetrahydro-4-quinazolinone
7-Chloro-2-phenyl-1-[2-(1-phenyl-4-piperazinyl)-ethyl]-1,2,3,4-tetrahydro-4-quinazolinone
8-Chloro-2-phenyl-1-[2-(1-phenyl-4-piperazinyl)-ethyl]-1,2,3,4-tetrahydro-4-quinazolinone
5-Methyl-2-phenyl-1-[2-(1-phenyl-4-piperazinyl)-ethyl]-1,2,3,4-tetrahydro-4-quinazolinone
6-Methyl-2-phenyl-1-[2-(1-phenyl-4-piperazinyl)-ethyl]-1,2,3,4-tetrahydro-4-quinazolinone
7-Methyl-2-phenyl-1-[2-(1-phenyl-4-piperazinyl)-ethyl]-1,2,3,4-tetrahydro-4-quinazolinone
8-Methyl-2-phenyl-1-[2-(1-phenyl-4-piperazinyl)-ethyl]-1,2,3,4-tetrahydro-4-quinazolinone
5-Formamido-2-phenyl-1-[2-(1-phenyl-4-piperazinyl)-ethyl]-1,2,3,4-tetrahydro-4-quinazolinone
6-Formamido-2-phenyl-1-[2-(1-phenyl-4-piperazinyl)-ethyl]-1,2,3,4-tetrahydro-4-quinazolinone
7-Formamido-2-phenyl-1-[2-(1-phenyl-4-piperazinyl)-ethyl]-1,2,3,4-tetrahydro-4-quinazolinone
8-Formamido-2-phenyl-1-[2-(1-phenyl-4-piperazinyl)-ethyl]-1,2,3,4-tetrahydro-4-quinazolinone
2-Phenyl-1-[2-(1-phenyl-4-piperazinyl)-ethyl]-6-trifluoromethyl-1,2,3,4-tetrahydro-4-quinazolinone
2-Phenyl-1-[2-(1-phenyl-4-piperazinyl)-ethyl]-7-trifluoromethyl-1,2,3,4-tetrahydro-4-quinazolinone
2-Phenyl-1-[2-(1-phenyl-4-piperazinyl)-ethyl]-1,2,3,4-tetrahydro-4-quinazolinone
2-Phenyl-1-[3-(1-phenyl-4-piperazinyl)-propyl]-1,2,3,4-tetrahydro-4-quinazolinone
1-[1-Methyl-2-(1-phenyl-4-piperazinyl)-ethyl]-2-phenyl-1,2,3,4-tetrahydroquinazolinone
d-1-[1-Methyl-2-(1-phenyl-4-piperazinyl)-ethyl]-2-phenyl-1,2,3,4-tetrahydro-4-quinazolinone
1-1[1-Methyl-2-(1-phenyl-4-piperazinyl)-ethyl]-2-phenyl-1,2,3,4-tetrahydro-4-quinazolinone
1-[2-Methyl-2-(1-phenyl-4-piperazinyl)-ethyl]-2-phenyl-1,2,3,4-tetrahydro-4-quinazolinone
d-1-[2-Methyl-2-(1-phenyl-4-piperazinyl)-ethyl]-2-phenyl-1,2,3,4-tetrahydro-4-quinazolinone
1-1-[2-Methyl-2-(1-phenyl-4-piperazinyl)-ethyl]-2-phenyl-1,2,3,4-tetrahydro-4-quinazolinone
1-[2-(1-[o-Chlorophenyl]-4-piperazinyl)-ethyl]-2-phenyl-1,2,3,4-tetrahydro-4-quinazolinone
1-[2-(1-[m-Chlorophenyl]-4-piperazinyl)-ethyl]-2-phenyl-1,2,3,4-tetrahydro-4-quinazolinone
1-[2-(1-[p-Chlorophenyl]-4-piperazinyl)-ethyl]-2-phenyl-1,2,3,4-tetrahydro-4-quinazolinone
1-[2-(1-[o-Aminophenyl]-4-piperazinyl)-ethyl]-2-phenyl-1,2,3,4-tetrahydro-4-quinazolinone
1-[2-(1-[m-Aminophenyl]-4-piperazinyl)-ethyl]-2-phenyl-1,2,3,4-tetrahydro-4-quinazolinone
1-[2-(1-[p-Aminophenyl]-4-piperazinyl)-ethyl]-2-phenyl-1,2,3,4-tetrahydro-4-quinazolinone
1-[2-(1[o-Methoxyphenyl]-4-piperazinyl)-ethyl]-2-phenyl-1,2,3,4-tetrahydro-4-quinazolinone
1-[2-(1-[m-Methoxyphenyl]-4-piperazinyl)-ethyl]-2-phenyl-1,2,3,4-tetrahydro-4-quinazolinone
1-[2-(1-[p-Methoxyphenyl]-4-piperazinyl)-ethyl]-2-phenyl-1,2,3,4-tetrahydro-4-quinazolinone
1-[2-(1-[o-Hydroxyphenyl]-4-piperazinyl)-ethyl]-2-phenyl-1,2,3,4-tetrahydro-4-quinazolinone
1-[2-(1-[m-Hydroxyphenyl]-4-piperazinyl)-ethyl]-2-phenyl-1,2,3,4-tetrahydro-4-quinazolinone
1-[2-(1-[p-Hydroxphenyl]-4-piperazinyl)-ethyl]-2-phenyl-1,2,3,4-tetrahydro-4-quinazolinone
2-Phenyl-1-[2-(1-[o-tolyl]-4-piperazinyl)-ethyl]-1,2,3,4-tetrahydro-4-quinazolinone
2-Phenyl-1-[2-(1-[m-tolyl]-4-piperazinyl)-ethyl]-1,2,3,4-tetrahydro-4-quinazolinone
2-Phenyl-1-[2-(1-[p-tolyl]-4-piperazinyl)-ethyl]-1,2,3,4-tetrahydro-4-quinazolinone
1-[3-(1-[o-Chlorophenyl]-4-piperazinyl)-propyl]-2-phenyl-1,2,3,4-tetrahydro-4-quinazolinone
1-[3-(1-[m-Chlorophenyl[-4-piperazinyl)-propyl]-2-phenyl-1,2,3,4-tetrahydro-4-quinazolinone
1-[3-(1-[p-Chlorophenyl]-4-piperazinyl)-propyl]-2-phenyl-1,2,3,4-tetrahydro-4-quinazolinone
1-[3-(1-[o-Aminophenyl]-4-piperazinyl)-propyl]-2-phenyl-1,2,3,4-tetrahydro-4-quinazolinone
1-[3-(1-[m-Aminophenyl]-4-piperazinyl)-propyl]-2-phenyl-1,2,3,4-tetrahydro-4-quinazolinone
1-[3-(1-[p-Aminophenyl]-4-piperazinyl)-propyl]-2-phenyl-1,2,3,4-tetrahydro-4-quinazolinone
1-[3-(1-[o-Methoxyphenyl]-4-piperazinyl)-propyl]-2-phenyl-1,2,3,4-tetrahydro-4-quinazolinone
1-[3-(1-[m-Methoxyphenyl]-4-piperazinyl)-propyl]-2-phenyl-1,2,3,4-tetrahydro-4-quinazolinone 1-[3-(1-[p-Methoxyphenyl]-4-piperazinyl)-propyl]-2-phenyl-1,2,3,4-tetrahydro-4-quinazolinone
1-[3-(1-[o-Hydroxyphenyl]-4-piperazinyl)-propyl]-2-phenyl-1,2,3,4-tetrahydro-4-quinazolinone
1-[3-(1-[m-Hydroxyphenyl]-4-piperazinyl)-propyl]-2-phenyl-1,2,3,4-tetrahydro-4-quinazolinone
1-[3-(1-[p-Hydroxyphenyl]-4-piperazinyl)-propyl]-2-phenyl-1,2,3,4-tetrahydro-4-quinazolinone
2-Phenyl-1-[3-(1-[o-tolyl]-4-piperazinyl)-propyl]-1,2,3,4-tetrahydro-4-quinazolinone
2-Phenyl-1-[3-(1-[m-tolyl]-4-piperazinyl)-propyl]-1,2,3,4-tetrahydro-4-quinazolinone
2-Phenyl-1-[3-(1-[p-tolyl]-4-piperazinyl)-propyl]-1,2,3,4-tetrahydro-4-quinazolinone
1-[1-Methyl-2-(1-[o-chlorophenyl]-4-piperazinyl)-ethyl]-2-phenyl-1,2,3,4-tetrahydro-4-quinazolinone
d-1-[1-Methyl-2-(1-[o-chlorophenyl]-4-piperazinyl)-ethyl]-2-phenyl-1,2,3,4-tetrahydro-4-quinazolinone
l-1-[1-Methyl-2-(1-[o-chlorophenyl]-4-piperazinyl)-ethyl]-2-phenyl-1,2,3,4-tetrahydro-4-quinazolinone
1-[1-Methyl-2-(1-[m-chlorophenyl]-4-piperazinyl)-ethyl]-2-phenyl-1,2,3,4-tetrahydro-4-quinazolinone
d-1-[1-Methyl-2-(1-[m-chlorophenyl]-4-piperazinyl)-ethyl]-2-phenyl-1,2,3,4-tetrahydro-4quinazolinone
l-1-[1-Methyl-2-(1-[m-chlorophenyl]-4-piperazinyl)-ethyl]-2-phenyl-1,2,3,4-tetrahydro-4-quinazolinone
1-[1-Methyl-2-(1-[p-chlorophenyl]-4-piperazinyl)-ethyl]-2-phenyl-1,2,3,4-tetrahydro-4-quinazolinone
d-1-[1-Methyl-2-(1-[p-chlorophenyl]-4-piperazinyl)-ethyl]-2-phenyl-1,2,3,4-tetrahydro-4-quinazolinone
l-1-[1-Methyl-2-(1-[p-chlorophenyl]-4-piperazinyl)-ethyl]-2-phenyl-1,2,3,4-tetrahydro-4-quinazolinone
1-[1-Methyl-2-(1-[o-aminophenyl]-4-piperazinyl)-ethyl]-2-phenyl-1,2,3,4-tetrahydro-4-quinazolinone
d-1-[1-Methyl-2-(1-[o-aminophenyl]-4-piperazinyl)-ethyl]-2-phenyl-1,2,3,4-tetrahydro-4-quinazolinone
l-1-[1-Methyl-2-(1-[o-aminophenyl]-4-piperazinyl)-ethyl]-2-phenyl-1,2,3,4-tetrahydro-4-quinazolinone
1-[1-Methyl-2-(1-[m-aminophenyl]-4-piperazinyl)-ethyl]-2-phenyl-1,2,3,4-tetrahydro-4-quinazolinone
d-1-(1-Methyl-2-(1-[m-aminophenyl]-4-piperazinyl)-ethyl]-2-phenyl-1,2,3,4-tetrahydro-4-quinazolinone
l-1-(1-Methyl-2-(1-[m-aminophenyl]-4-piperazinyl)-ethyl]-2-phenyl-1,2,3,4-tetrahydro-4-quinazolinone
1-[1-Methyl-2-(1-[p-aminophenyl]-4-piperazinyl)-ethyl]-2-phenyl-1,2,3,4-tetrahydro-4-quinazolinone
d-1-[1-Methyl-2-(1-[p-aminophenyl]-4-piperazinyl)-ethyl]-2-phenyl-1,2,3,4-tetrahydro-4-quinazolinone
l-1-[1-Methyl-2-(1-[p-aminophenyl]-4-piperazinyl)-ethyl]-2-phenyl-1,2,3,4-tetrahydro-4-quinazolinone
1-[1-Methyl-2-(1-[o-methoxyphenyl]-4-piperazinyl)-ethyl]-2-phenyl-1,2,3,4-tetrahydro-4quinazolinone
d-1-[1-Methyl-2-(1-[o-methoxyphenyl]-4-piperazinyl)-ethyl]-2-phenyl-1,2,3,4-tetrahydro-4-quinazolinone
l-1-[1-Methyl-2-(1-[o-methoxyphenyl]-4-piperazinyl)-ethyl]-2-phenyl-1,2,3,4-tetrahydro-4-quinazolinone
1-(1-Methyl-2-(1-[m-methoxyphenyl]-4-piperazinyl)-ethyl]-2-phenyl-1,2,3,4-tetrahydro-4-quinazolinone
d-1-[1-Methyl-2-(1-[m-methoxyphenyl]-4-piperazinyl)-ethyl]-2-phenyl-1,2,3,4-tetrahydro-4-quinazolinone
l-1-[1-Methyl-2-(1-[m-methoxyphenyl]-4-piperazinyl)-ethyl]-2-phenyl-1,2,3,4-tetrahydro-4-quinazolinone
1-[1-Methyl-2-(1-[p-methoxyphenyl]-4-piperazinyl)-ethyl]-2-phenyl-1,2,3,4-tetrahydro-4-quinazolinone
d-1-[1-Methyl-2-(1-[p-methoxyphenyl]-4-piperazinyl)-ethyl]-2-phenyl-1,2,3,4-tetrahydro-4-quinazolinone
l-1-[1-Methyl-2-(1-[p-methoxyphenyl]-4-piperazinyl)-ethyl]-2-phenyl-1,2,3,4-tetrahydro-4-quinazolinone
1-[1-Methyl-2-(1-[o-hydroxyphenyl]-4-piperazinyl)-ethyl]-2-phenyl-1,2,3,4-tetrahydro-4-quinazolinone
d-1-[1-Methyl-2-(1-[o-hydroxyphenyl]-4-piperazinyl)-ethyl]-2-phenyl-1,2,3,4-tetrahydro-4-quinazolinone
l-1-[1-Methyl-2-(1-[o-hydroxyphenyl]-4-piperazinyl)-ethyl]-2-phenyl-1,2,3,4-tetrahydro-4-quinazolinone
1-[1-Methyl-2-(1-[m-hydroxyphenyl]-4-piperazinyl)-ethyl]-2-phenyl-1,2,3,4-tetrahydro-4-quinazolinone
d-1-[1-Methyl-2-(1-[m-hydroxyphenyl]-4-piperazinyl)-ethyl]-2-phenyl-1,2,3,4-tetrahydro-4quinazolinone
l-1-[1-Methyl-2-(1-[m-hydroxyphenyl]-4-piperazinyl)-ethyl-2-phenyl-1,2,3,4-tetrahydro-4-quinazolinone
1-[1-Methyl-2-(1-[p-hydroxyphenyl]-4-piperazinyl)-ethyl]-2-phenyl-1,2,3,4-tetrahydro-4-quinazolinone
d-1-[1-Methyl-2-(1-[p-hydroxyphenyl]-4-piperazinyl)-ethyl]-2-phenyl-1,2,3,4-tetrahydro-4quinazolinone
l-1-[1-Methyl-2-(1-[p-hydroxyphenyl]-4-piperazinyl)-ethyl]-2-phenyl-1,2,3,4-tetrahydro-4-quinazolinone
1-[1-Methyl-2-(1-[o-tolyl]-4-piperazinyl)-ethyl]-2-phenyl-1,2,3,4-tetrahydro-4-quinazolinone
d-1-[1-Methyl-2-(1-[o-tolyl]-4-piperazinyl)-ethyl]-2-phenyl-1,2,3,4-tetrahydro-4-quinazolinone
l-1-[1-Methyl-2-(1-[o-tolyl]-4-piperazinyl)-ethyl]-2-phenyl-1,2,3,4-tetrahydro-4-quinazolinone
1-[1-Methyl-2-(1-[m-tolyl]-4-piperazinyl)-ethyl]-2-phenyl-1,2,3,4-tetrahydro-4-quinazolinone
d-1-[1-Methyl-2-(1-[m-tolyl]-4-piperazinyl)-ethyl]-2-phenyl-1,2,3,4-tetrahydro-4-quinazolinone
l-1-[1-Methyl-2-(1-[m-tolyl]-4-piperazinyl)-ethyl]-2-phenyl-1,2,3,4-tetrahydro-4-quinazolinone
1-[1-Methyl-2-(1-[p-tolyl]-4-piperazinyl)-ethyl]-2-phenyl-1,2,3,4-tetrahydro-4-quinazolinone
d-1-[1-Methyl-2-(1-[p-tolyl]-4-piperazinyl)-ethyl]-2-phenyl-1,2,3,4-tetrahydro-4-quinazolinone
l-1-[1-Methyl-2-(1-[p-tolyl]-4-piperazinyl)-ethyl]-2-phenyl-1,2,3,4-tetrahydro-4-quinazolinone
1-[2-Methyl-2-(1-[o-chlorophenyl]-4piperazinyl)-ethyl]-2-phenyl-1,2,3,4-tetrahydro-4-quinazolinone
d-1-[2-Methyl-2-(1-[o-chlorophenyl]-4-piperazinyl)-ethyl]-2-phenyl-1,2,3,4-tetrahydro-4-quinazolinone
l-1-[2-Methyl-2-(1-[o-chlorophenyl]-4-piperazinyl)-ethyl]-2-phenyl-1,2,3,4-tetrahydro-4-quinazolinone
1-[2-Methyl-2-(1-[m-chlorophenyl]-4-piperazinyl)-ethyl]-2-phenyl-1,2,3,4-tetrahydro-4-quinazolinone
d-1-[2-Methyl-2-(1-[m-chlorophenyl]-4-piperazinyl)-ethyl]-2-phenyl-1,2,3,4-tetrahydro-4-quinazolinone
l-1-[2-Methyl-2-(1-[m-chlorophenyl]-4-piperazinyl)-ethyl]-2-phenyl-1,2,3,4-tetrahydro-4-quinazolinone
1-[2-Methyl-2-(1-[p-chlorophenyl]-4-piperazinyl)-ethyl]-2-phenyl-1,2,3,4-tetrahydro-4-quinazolinone
d-1-[2-Methyl-2-(1-[p-chlorophenyl]-4-piperazinyl)-ethyl]-2-phenyl-1,2,3,4-tetrahydro-4-quinazolinone
l-1-[2-Methyl-2-(1-[p-chlorophenyl]-4-piperazinyl)-ethyl]-2-phenyl-1,2,3,4-tetrahydro-4-quinazolinone
1-[2-Methyl-2-(1-[o-aminophenyl]-4-piperazinyl)-ethyl]-2-phenyl-1,2,3,4-tetrahydro-4-quinazolinone
d-1-[2-Methyl-2-(1-[o-aminophenyl]-4-piperazinyl)-ethyl]-2-phenyl-1,2,3,4-tetrahydro-4-quinazolinone
l-1-[2-Methyl-2-(1-[o-aminophenyl]-4-piperazinyl)-ethyl]-2-phenyl-1,2,3,4-tetrahydro-4-quinazolinone
1-[2-Methyl-2-(1-[m-aminophenyl]-4-piperazinyl)-ethyl]-2-phenyl-1,2,3,4-tetrahydro-4-quinazolinone
d-1-[2-Methyl-2-(1-[m-aminophenyl]-4-piperazinyl)-ethyl]-2-phenyl-1,2,3,4-tetrahydro-4-quinazolinone
l-1-[2-Methyl-2-(1-[m-aminophenyl]-4-piperazinyl)-ethyl]-2-phenyl-1,2,3,4-tetrahydro-4-quinazolinone
1-[2-Methyl-2-(1-[p-aminophenyl]-4-piperazinyl)-ethyl]-2-phenyl-1,2,3,4-tetrahydro-4-quinazolinone d-1-[2-Methyl-2-(1-[p-aminophenyl]-4-piperazinyl)-ethyl]-2-phenyl-1,2,3,4-tetrahydro-4-quinazolinone
l-1[2-Methyl-2-(1-[p-aminophenyl]-4-piperazinyl)-ethyl]-2-phenyl-1,2,3,4-tetrahydro-4-quinazolinone
1-[2-Methyl-2-(1-[o-methoxyphenyl]-4-piperazinyl)-ethyl]-2-phenyl-1,2,3,4-tetrahydro-4-quinazolinone
d-1-[2-Methyl-2-(1-[o-methoxyphenyl]-4-piperazinyl)-ethyl]-2-phenyl-1,2,3,4-tetrahydro-4-quinazolinone
l-1-[2-Methyl-2-(1-[o-methoxyphenyl]-4-piperazinyl)-ethyl]-2-phenyl-1,2,3,4-tetrahydro-4-quinazolinone
1-[2-Methyl-2-(1-[m-methoxyphenyl]-4-piperazinyl)-ethyl]-2-phenyl-1,2,3,4-tetrahydro-4-quinazolinone
d-1-[2-Methyl-2-(1-[m-methoxyphenyl]-4-piperazinyl)-ethyl]-2-phenyl-1,2,3,4-tetrahydro-4-quinazolinone
l-1-[2-Methyl-2-(1-[m-methoxyphenyl]-4-piperazinyl)-ethyl]-2-phenyl-1,2,3,4-tetrahydro-4-quinazolinone
1-[2-Methyl-2-(1-[p-methoxyphenyl]-4-piperazinyl)-ethyl]-2-phenyl-1,2,3,4-tetrahydro-4-quinazolinone
d-1-[2-Methyl-2-(1-[p-methoxyphenyl]-4-piperazinyl)-ethyl]-2-phenyl-1,2,3,4-tetrahydro-4-quinazolinone
l-1-[2-Methyl-2-(1-[p-methoxyphenyl]-4-piperazinyl(-ethyl]-2-phenyl-1,2,3,4-tetrahydro-4-quinazolinone
1-[2-Methyl-2-(1-[o-hydroxyphenyl]-4-piperazinyl)-ethyl]-2-phenyl-1,2,3,4-tetrahydro-4-quinazolinone
d-1-[2-Methyl-2-(1-[o-hydroxyphenyl]-4-piperazinyl)-ethyl]-2-phenyl-1,2,3,4-tetrahydro-4-quinazolinone
l-1-[2-Methyl-2-(1-[o-hydroxyphenyl]-4-piperazinyl)-ethyl]-2-phenyl-1,2,3,4-tetrahydro-4-quinazolinone
1-[2-Methyl-2-(1-[m-hydroxyphenyl]-4-piperazinyl)-ethyl]-2-phenyl-1,2,3,4-tetrahydro-4-quinazolinone
d-1-[2-Methyl-2-(1-[m-hydroxyphenyl]-4-piperazinyl)-ethyl]-2-phenyl-1,2,3,4-tetrahydro-4-quinazolinone
l-1-[2-Methyl-2-(1-[m-hydroxyphenyl]-4-piperazinyl)-ethyl]-2-phenyl-1,2,3,4-tetrahydro-4-quinazolinone
1-[2-Methyl-2-(1-[p-hydroxyphenyl]-4-piperazinyl)-ethyl]-2-phenyl-1,2,3,4-tetrahydro-4-quinazolinone
d-1-[2-Methyl-2-(1-[p-hydroxyphenyl]-4-piperazinyl)-ethyl]-2-phenyl-1,2,3,4-tetrahydro-4-quinazolinone
l-1-[2-Methyl-2-(1-[p-hydroxyphenyl]-4-piperazinyl)-ethyl]-2-phenyl-1,2,3,4-tetrahydro-4-quinazolinone
1-[2-Methyl-2-(1-[o-tolyl]-4-piperazinyl)-ethyl]-2-phenyl-1,2,3,4-tetrahydro-4-quinazolinone
d-1-[2-Methyl-2-(1-[o-tolyl]-4-piperazinyl)-ethyl]-2-2-phenyl-1,2,3,4-tetrahydro-4-quinazolinone
l-1-[2-Methyl-2-(1-[o-tolyl]-4-piperazinyl)-ethyl]-2-phenyl-1,2,3,4-tetrahydro-4-quinazolinone
1-[2-Methyl-2-(1-[m-tolyl]-4-piperazinyl)-ethyl]2-phenyl-1,2,3,4-tetrahydro-4-quinazolinone
d-1-[2-Methyl-2-(1-[m-tolyl]-4-piperazinyl)-ethyl]-2-phenyl-1,2,3,4-tetrahydro-4-quinazolinone
l-1-[2-Methyl-2-(1-[m-tolyl]-4-piperazinyl)-ethyl]-2-phenyl-1,2,3,4-tetrahydro-4-quinazolinone
1-[2-Methyl-2-(1-[p-tolyl]-4-piperazinyl)-ethyl]-2-phenyl-1,2,3,4-tetrahydro-4-quinazolinone
d-1-[2-Methyl-2-(1-[p-tolyl]-4-piperazinyl)-ethyl]-2-phenyl-1,2,3,4-tetrahydro-4-quinazolinone
l-1-[2-Methyl-2-(1-[p-tolyl]-4-piperazinyl)-ethyl]-2-phenyl-1,2,3,4-tetrahydro-4-quinazolinone
2-Phenyl-1-[2-(1-phenyl-2-methyl-4-piperazinyl)-ethyl]-1,2,3,4-tetrahydro-4-quinazolinone
2-Benzyl-1-[1-methyl-2-(1-phenyl-4-piperazinyl)-ethyl]-1,2,3,4-tetrahydro-4-quinazolinone
2-Benzyl-1-[2-(1-[p-hydroxyphenyl]-4-piperazinyl)-ethyl]-1,2,3,4-tetrahydro-4-quinazolinone
2-Benzyl-1-[2-(1-[p-methoxyphenyl]-4-piperazinyl)-ethyl]-1,2,3,4-tetrahydro-4-quinazolinone
6-Amino-2-benzyl-1-[2-(1-phenyl-4-piperazinyl)-ethyl]-1,2,3,4-tetrahydro-4-quinazolinone
6-Amino-1-[2-(1-phenyl-4-piperazinyl)-ethyl]-2-(2-pryidylmethyl)-1,2,3,4-tetrahydro-4-quinazolinone
6-Amino-1-[1-methyl-2-(1-phenyl-4-piperazinyl)-ethyl]-2-(2-pyridylmethyl)-1,2,3,4-tetrahydro-4-quinazolinone
3-Methyl-2-phenyl-1-[2-(1-phenyl-4-piperazinyl)-ethyl]-1,2,3,4-tetrahydro-4-quinazolinone
2-Phenyl-1-[2-(1-piperazinyl)-ethyl]-1,2,3,4-tetrahydro-4-quinazolinone
1-[2-(1-Methyl-4-piperazinyl-ethyl]-2-phenyl-1,2,3,4-tetrahydro-4-quinazolinone
1-[2-(1-Benzyl-4-piperazinyl)-ethyl]-2-phenyl-1,2,3,4-tetrahydro-4-quinazolinone
1-[2-(1-Phenethyl-4-piperazinyl)-ethyl]-2-phenyl-1,2,3,4-tetrahydro-4-quinazolinone
1-[2-(1-[p-aminophenethyl]-4-piperazinyl)-ethyl]-2-phenyl-1,2,3,4-tetrahydro-4-quinazolinone
1-[1-Methyl-2-(1-piperazinyl)-ethyl]-2-phenyl-1,2,3,4-tetrahydro-4-quinazolinone
1-[1-Methyl-2-(1-methyl-4-piperazinyl)-ethyl]-2-phenyl-1,2,3,4-tetrahydro-4-quinazolinone
1-[1-Methyl-2-(1-benzyl-4-piperazinyl)-ethyl]-2-phenyl-1,2,3,4-tetrahydro-4-quinazolinone
1-[1-Methyl-2-(1-phenethyl-4-piperazinyl)-ethyl]-2-phenyl-1,2,3,4-tetrahydro-4-quinazolinone
1-[1-Methyl-2-(1-[p-aminophenethyl]-4-piperazinyl)-ethyl]-2-phenyl-1,2,3,4-tetrahydro-4-quinazolinone
6-Amino-1-[1-methyl-2-(1-piperazinyl)-ethyl]-2-phenyl-1,2,3,4-tetrahydro-4-quinazolinone
6-Amino-1-[1-methyl-2-(1-methyl-4-piperazinyl)-ethyl]-2-phenyl-1,2,3,4-tetrahydro-4-quinazolinone
6-Amino-1-[1-methyl-2-(1-benzyl-4-piperazinyl)-ethyl]-2-phenyl-1,2,3,4-tetrahydro-4-quinazolinone
6-Amino-1-[1-methyl-2-(1-phenethyl-4-piperazinyl)-ethyl]-2-phenyl-1,2,3,4-tetrahydro-4-quinazolinone
6-Amino-1-[1-methyl-2-(1-[p-aminophenethyl]-4-piperazinyl)-ethyl]-2-phenyl-1,2,3,4-tetrahydro-4-quinazolinone Typical examples of analgesic intermediates of this invention are as follows:

2-[2-(4-[1-Phenyl]-piperazinyl)-ethylamino]-benzamide
3-Amino-2-[2-(1-phenyl-4-piperazinyl)-ethylamino]-benzamide
4-Amino-2-[2-(1-phenyl-4-piperazinyl)-ethalamino]-benzamide
5-Amino-2-[2-(1-phenyl-4-piperazinyl)-ethylamino]-benzamide
6-Amino-2-[2-(1-phenyl-4-piperazinyl)-ethylamino]-benzamide
3-Methoxy-2-[2-(1-phenyl-4-piperazinyl)-ethylamino]-benzamide
4-Methoxy-2-[2-(1-phenyl-4-piperazinyl)-ethylamino]-benzamide
5-Methoxy-2-[2-(1-phenyl-4-piperazinyl)-ethylamino]-benzamide
6-Methoxy-2-[2-(1-phenyl-4-piperazinyl)-ethylamino]-benzamide
3-Hydroxy-2-[2-(1-phenyl-4-piperazinyl)-ethylamino]-benzamide
4-Hydroxy-2-[2-(1-phenyl-4-piperazinyl)-ethylamino]-benzamide
5-Hydroxy-2-[2-(1-phenyl-4-piperazinyl)-ethylamino]-benzamide
6-Hydroxy-2-[2-(1-phenyl-4-piperazinyl)-ethylamino]-benzamide 3-Chloro-2-[2-(1-phenyl-4-piperazinyl)-ethylamino]-benzamide
4-Chloro-2-[2-(1-phenyl-4-piperazinyl)-ethylamino]-benzamide
5-Chloro-2-[2-(1-phenyl-4-piperazinyl)-ethylamino]-benzamide
6-Chloro-2-[2-(1-phenyl-4-piperazinyl)-ethylamino]-benzamide
3-Methyl-2-[2-(1-phenyl-4-piperazinyl)-ethylamino]-benzamide
4-Methyl-2-[2-(1-phenyl-4-piperazinyl)-ethylamino]-benzamide
5-Methyl-2-[2-(1-phenyl-4-piperazinyl)-ethylamino]-benzamide
6-Methyl-2-[2-(1-phenyl-4-piperazinyl)-ethylamino]-benzamide
3-Formamido-2-[2-(1-phenyl-4-piperazinyl)-ethylamino]-benzamide
4-Formamido-2-[2-(1-phenyl-4-piperazinyl)-ethylamino]-benzamide
5-Formamido-2-[2-(1-phenyl-4-piperazinyl)-ethylamino]-benzamide
6-Formamido-2-[2-(1-phenyl-4-piperazinyl)-ethylamino]-benzamide
2-[2-(1-Phenyl-4-piperazinyl)-ethylamino]-3-trifluoromethyl-benzamide
2-[2-(1-Phenyl-4-piperazinyl)-ethylamino]-4-trifluoromethyl-benzamide
2-[3-(1-Phenyl-4-piperazinyl)-propylamino]-benzamide
2-[1-Methyl-2-(1-phenyl-4-piperazinyl)-ethylamino]-benzamide
d-2-[1-Methyl-2-(1-phenyl-4-piperazinyl)-ethylamino]-benzamide
l-2-[1-Methyl-2-(1-phenyl-4-piperazinyl)-ethylamino]-benzamide
2-[2-Methyl-2-(1-phenyl-4-piperazinyl)-ethylamino]-benzamide
d-2-[2-Methyl-2-(1-phenyl-4-piperazinyl)-ethylamino]-benzamide
l-2-[2-Methyl-2-(1-phenyl-4-piperazinyl)-ethylamino]-benzamide
2-[2-(1-[o-Chlorophenyl]-4-piperazinyl)-ethylamino]-benzamide
2-[2-(1-[m-Chlorophenyl]-4-piperazinyl)-ethylamino]-benzamide
2-[2-(1-[p-Chlorophenyl]-4-piperazinyl)-ethylamino]-benzamide
2-[2-(1-[o-Aminophenyl]-4-piperazinyl)-ethylamino]-benzamide
2-[2-(1-[m-Aminophenyl]-4-piperazinyl)-ethylamino]-benzamide
2-[2-(1-[p-Aminophenyl]-4-piperazinyl)-ethylamino]-benzamide
2-[2-(1-[o-Methoxyphenyl]-4-piperazinyl)-ethylamino]-benzamide
2-[2-(1-[m-Methoxyphenyl]-4-piperazinyl)-ethylamino]-benzamide
2-[2-(1-[p-Methoxyphenyl]-4-piperazinyl)-ethylamino]-benzamide
2-[2-(1-[o-Hydroxyphenyl]-4-piperazinyl)-ethylamino]-benzamide
2-[2-(1-[m-Hydroxyphenyl]-4-piperazinyl)-ethylamino]-benzamide
2-[2-(1-[p-Hydroxyphenyl]-4-piperazinyl)-ethylamino]-benzamide
2-[2-(1-[o-Tolyl]-4-piperazinyl)-ethylamino]-benzamide
2-[2-(1-[m-Tolyl]-4-piperazinyl)-ethylamino]-benzamide
2-[2-(1-[p-Tolyl]-4-piperazinyl)-ethylamino]-benzamide
2-[3-(1-[o-Chlorophenyl]-4-piperazinyl)-propylamino]-benzamide
2-[3-(1-[m-Chlorophenyl]-4-piperazinyl)-propylamino]-benzamide
2-[3-(1-[p-Chlorophenyl]-4-piperazinyl)-propylamino]-benzamide
2-[3-(1-[o-Aminophenyl]-4-piperazinyl)-propylamino]-benzamide
2-[3-(1-[m-Aminophenyl]-4-piperazinyl)-propylamino]-benzamide
2-[3-(1-[p-Aminophenyl]-4-piperazinyl)-propylamino]-benzamide
2-[3-(1-[o-Methoxyphenyl]-4-piperazinyl)-propylamino]-benzamide
2-[3-(1-[m-Methoxyphenyl]-4-piperazinyl)-propylamino]-benzamide
2-[3-(1-[p-Methoxyphenyl]-4-piperazinyl)-propylamino]-benzamide
2-[3-(1-[o-Hydroxyphenyl]-4-piperazinyl)-propylamino]-benzamide
2-[3-(1-[m-Hydroxyphenyl]-4-piperazinyl)-propylamino]-benzamide
2-[3-(1-[p-Hydroxyphenyl]-4-piperazinyl)-propylamino]-benzamide
2-[3-(1-[o-Tolyl]-4-piperazinyl)-propylamino]-benzamide
2-[3-(1-[m-Tolyl]-4-piperazinyl)-propylamino]-benzamide
2-[3-(1-[p-Tolyl]-4-piperazinyl)-propylamino]-benzamide
2-[1-Methyl-2-(1-[o-chlorophenyl]-4-piperazinyl)-ethylamino]-benzamide
d-2-[1-Methyl-2-(1-[o-chlorophenyl]-4-piperazinyl)-ethylamino]-benzamide
l-2-[1-Methyl-2-(1-[o-chlorophenyl]-4-piperazinyl)-ethylamino]-benzamide
2-[1-Methyl-2-(1-[m-chlorophenyl]-4-piperazinyl)-ethylamino]-benzamide
d-2-[1-Methyl-2-(1-[m-chlorophenyl]-4-piperazinyl)-ethylamino]-benzamide
l-2-[1-Methyl-2-(1-[m-chlorophenyl]-4-piperazinyl)-ethylamino]-benzamide
2-[1-Methyl-2-(1-[p-chlorophenyl]-4-piperazinyl)-ethylamino]-benzamide
d-2-[1-Methyl-2-(1-[p-chlorophenyl]-4-piperazinyl)-ethylamino]-benzamide
l-2-[1-Methyl-2-(1-[p-chlorophenyl]-4-piperazinyl)-ethylamino]-benzamide
2-[1-Methyl-2-(1-[o-Aminophenyl]-4-piperazinyl)-ethylamino]-benzamide
d-2-[1-Methyl-2-(1-[o-Aminophenyl]-4-piperazinyl)-ethylamino]-benzamide
l-2-[1-Methyl-2-(1-[o-Aminophenyl]-4-piperazinyl)-ethylamino]-benzamide
2-[1-Methyl-2-(1-[m-Aminophenyl]-4-piperazinyl)-ethylamino]-benzamide
d-2-[1-Methyl-2-(1-[m-Aminophenyl]-4-piperazinyl)-ethylamino]-benzamide
l-2-[1-Methyl-2-(1-[m-Aminophenyl]-4-piperazinyl)-ethylamino]-benzamide
2-[1-Methyl-2-(1-[p-Aminophenyl]-4-piperazinyl)-ethylamino]-benzamide
d-2-[1-Methyl-2-(1-[p-Aminophenyl]-4-piperazinyl)-ethylamino]-benzamide
l-2-[1-Methyl-2-(1-[p-Aminophenyl]-4-piperazinyl)-ethylamino]-benzamide 2-[1-Methyl-2-(1-[o-methoxyphenyl]-4-piperazinyl)-ethylamino]-benzamide
d-2-[1-Methyl-2-(1-[o-methoxyphenyl]-4-piperazinyl)-ethylamino]-benzamide
l-2-[1-Methyl-2-(1-[o-methoxyphenyl]-4-piperazinyl)-ethylamino]-benzamide
2-[1-Methyl-2-(1-[m-methoxyphenyl]-4-piperazinyl)-ethylamino]-benzamide
d-2-[1-Methyl-2-(1-[m-methoxyphenyl]-4-piperazinyl)-ethylamino]-benzamide
l-2-[1-Methyl-2-(1-[m-methoxyphenyl]-4-piperazinyl)-ethylamino]-benzamide
2-[1-Methyl-2-(1-[p-methoxyphenyl]-4-piperazinyl)-ethylamino]-benzamide
d-2-[1-Methyl-2-(1-[p-methoxyphenyl]-4-piperazinyl)-ethylamino]-benzamide
l-2-[1-Methyl-2-(1-[p-methoxyphenyl]-4-piperazinyl)-ethylamino]-benzamide
2-[1-Methyl-2-(1-[o-hydroxyphenyl]-4-piperazinyl)-ethylamino]-benzamide
d-2-[1-Methyl-2-(1-[o-hydroxyphenyl]-4-piperazinyl)-ethylamino]-benzamide
l-2-[1-Methyl-2-(1-[o-hydroxyphenyl]-4-piperazinyl)-ethylamino]-benzamide
2-[1-Methyl-2-(1-[m-hydroxyphenyl]-4-piperazinyl)-ethylamino]-benzamide
d-2-[1-Methyl-2-(1-[m-hydroxyphenyl]-4-piperazinyl)-ethylamino]-benzamide
l-2-[1-Methyl-2-(1-[m-hydroxyphenyl]-4-piperazinyl)-ethylamino]-benzamide
2-[1-Methyl-2-(1-[p-hydroxyphenyl]-4-piperazinyl)-ethylamino]-benzamide
d-2-[1-Methyl-2-(1-[p-hydroxyphenyl]-4-piperazinyl)-ethylamino]-benzamide
l-2-[1-Methyl-2-(1-[p-hydroxyphenyl]-4-piperazinyl)-ethylamino]-benzamide
2-[1-Methyl-2-(1-[o-tolyl]-4-piperazinyl)-ethylamino]-benzamide
d-2-[1-Methyl-2-(1-[o-tolyl]-4-piperazinyl)-ethylamino]-benzamide
l-2-[1-Methyl-2-(1-[o-tolyl]-4-piperazinyl)-ethylamino]-benzamide
2-[1-Methyl-2-(1-[m-tolyl]-4-piperazinyl)-ethylamino]-benzamide
d-2-[1-Methyl-2-(1-[m-tolyl]-4-piperazinyl)-ethylamino]-benzamide
l-2-[1-Methyl-2-(1-[m-tolyl]-4-piperazinyl)-ethylamino]-benzamide
2-[1-Methyl-2-(1-[p-tolyl]-4-piperazinyl)-ethylamino]-benzamide
d-2-[1-Methyl-2-(1-[p-tolyl]-4-piperazinyl)-ethylamino]-benzamide
l-2-[1-Methyl-2-(1-[p-tolyl]-4-piperazinyl)-ethylamino]-benzamide
2-[2-Methyl-2-(1-[o-chlorophenyl]-4-piperazinyl)-ethylamino]-benzamide
d-2-[2-Methyl-2-(1-[o-chlorophenyl]-4-piperazinyl)-ethylamino]-benzamide
l-2-[2-Methyl-2-(1-[o-chlorophenyl]-4-piperazinyl)-ethylamino]-benzamide
2-[2-Methyl-2-(1-[m-chlorophenyl]-4-piperazinyl)-ethylamino]-benzamide
d-2-[2-Methyl-2-(1-[m-chlorophenyl]-4-piperazinyl)-ethylamino]-benzamide
l-2-[2-Methyl-2-(1-[m-chlorophenyl]-4-piperazinyl)-ethylamino]-benzamide
2-[2-Methyl-2-(1-[p-chlorophenyl]-4-piperazinyl)-ethylamino]-benzamide
d-2-[2-Methyl-2-(1-[p-chlorophenyl]-4-piperazinyl)-ethylamino]-benzamide
l-2-[2-Methyl-2-(1-[p-chlorophenyl]-4-piperazinyl)-ethylamino]-benzamide
2-[2-Methyl-2-(1-[o-aminophenyl]-4-piperazinyl)-ethylamino]-benzamide
d-2-[2-Methyl-2-(1-[o-aminophenyl]-4-piperazinyl)-ethylamino]-benzamide
l-2-[2-Methyl-2-(1-[o-aminophenyl]-4-piperazinyl)-ethylamino]-benzamide
2-[2-Methyl-2-(1-[m-aminophenyl]-4-piperazinyl)-ethylamino]-benzamide
d-2-[2-Methyl-2-(1-[m-aminophenyl]-4-piperazinyl)-ethylamino]-benzamide
l-2-[2-Methyl-2-(1-[m-aminophenyl]-4-piperazinyl)-ethylamino]-benzamide
2-[2-Methyl-2-(1-[p-aminophenyl]-4-piperazinyl)-ethylamino]-benzamide
d-2-[2-Methyl-2-(1-[p-aminophenyl]-4-piperazinyl)-ethylamino]-benzamide
l-2-[2-Methyl-2-(1-[p-aminophenyl]-4-piperazinyl)-ethyalamino]-benzamide
2-[2-Methyl-2-(1-[o-methoxyphenyl]-4-piperazinyl)-ethylamino]-benzamide
d-2-[2-Methyl-2-(1-[o-methoxyphenyl]-4-piperazinyl)-ethylamino]-benzamide
l-2-[2-Methyl-2-(1-[o-methoxyphenyl]-4-piperazinyl)-ethylamino]-benzamide
2-[2-Methyl-2-(1-[m-methoxyphenyl]-4-piperazinyl)-ethylamino]-benzamide
d-2-[2-Methyl-2-(1-[m-methoxyphenyl]-4-piperazinyl)-ethylamino]-benzamide
l-2-[2-Methyl-2-(1-[m-methoxyphenyl]-4-piperazinyl)-ethylamino]-benzamide
2-[2-Methyl-2-(1-[p-methoxyphenyl]-4-piperazinyl)-ethylamino]-benzamide
d-2-[2-Methyl-2-(1-[p-methoxyphenyl]-4-piperazinyl)-ethylamino]-benzamide
l-2-[2-Methyl-2-(1-[p-methoxyphenyl]-4-piperazinyl)-ethylamino]-benzamide
2-[2-Methyl-2-(1-[p-hydroxyphenyl]-4-piperazinyl)-ethylamino]-benzamide
d-2-[2-Methyl-2-(1-[o-hydroxylphenyl]-4-piperazinyl)-ethyalmino]-benzamide
l-2-[2-Methyl-2-(1-[o-hydroxyphenyl]-4-piperazinyl)-ethylamino]-benzamide
2-[2-Methyl-2-(1-[m-hydroxyphenyl]-4-piperazinyl)-ethylamino]-benzamide
d-2-[2-Methyl-2-(1-[m-hydroxyphenyl]-4-piperazinyl)-ethyalmino]-benzamide
l-2-[2-Methyl-2-(1-[m-hydroxyphenyl]-4-piperazinyl)-ethylamino]-benzamide
2-[2-Methyl-2-(1-[p-hydroxyphenyl]-4-piperazinyl)-ethylamino]-benzamide
d-2-[2-Methyl-2-(1-[p-hydroxyphenyl]-4-piperazinyl)-ethylamino]-benzamide
l-2-[2-Methyl-2-(1-[p-hydroxyphenyl]-4-piperazinyl)-ethylamino]-benzamide
2-[2-Methyl-2-(1-[o-tolyl]-4-piperazinyl)-ethylamino]-benzamide
d-2-[2-Methyl-2-(1-[o-tolyl]-4-piperazinyl)-ethyalmino]-benzamide
l-2-[2-Methyl-2-(1-[o-tolyl]-4-piperazinyl)-ethylamino]-benzamide
2-[2-Methyl-2-(1-[m-tolyl]-4-piperazinyl)-ethylamino]-benzamide
d-2-[2-Methyl-2-(1-[m-tolyl]-4-piperazinyl)-ethylamino]-benzamide l-2-[2-Methyl-2-(1-[m-tolyl]-4-piperazinyl)-ethylamino]-benzamide
2-[2-Methyl-2-(1-[p-tolyl]-piperazinyl)-ethylamino]-benzamide
d-2-[2-Methyl-2-(1-[p-tolyl]-4-piperazinyl)-ethylamino]-benzamide
l-2-[2-Methyl-2-(1-[p-tolyl]-4-piperazinyl)-ethylamino]-benzamide
2-[2-(2-Methyl-1-phenyl-4-piperazinyl)-ethylamino]-benzamide
N-Methyl-2-[2-(1-phenyl-4-piperazinyl)-ethylamino]-benzamide
2-[2-(1-Piperazinyl)-ethylamino]-benzamide
2-[2-(1-Methyl-4-piperazinyl)-ethylamino]-benzamide
2-[2-(1-Benzyl-4-piperazinyl)-ethylamino]-benzamide
2-[2-(1-Phenethyl-4-piperazinyl)-ethylamino]-benzamide
2-[2-(1-[p-Aminophenethyl]-4-piperazinyl)-ethylamino]-benzamide
2-(1-Methyl-2-(1-piperazinyl)-ethylamino]-benzamide
2-[1-Methyl-2-(1-methyl-4-piperazinyl)-ethylamino]-benzamide
2-[1-Methyl-2-(1-benzyl-4-piperazinyl)-ethylamino]-benzamide
2-[1-Methyl-2-(1-phenethyl-4-piperazinyl)-ethylamino]-benzamide
2-[1--Methyl-2-(1-[p-aminophenethyl]-4-piperazinyl)-ethylamino]-benzamide
5-Amino-2-[1-methyl-2-(1-piperazinyl)-ethylamino]-benzamide
5-Amino-2-[1-methyl-2-(1-methyl-4-piperazinyl)-ethylamino]-benzamide
5-Amino-2-[1-methyl-2-(1-benzyl-4-piperazinyl)-ethylamino]-benzamide
5-Amino-2-[1-mmethyl-2-(1-phenethyl-4-piperazinyl)-ethylamino]-benzamide
5-Amino-2-[1-methyl-2-(1-[p-aminophenethyl]-4-piperazinyl]-ethylamino]-benzamide
5-Amino-2-[1-methyl-2-(1-phenyl-4-piperazinyl)-ethylamino]-benzamide
2-[N-Benzoyl-2-(1-phenyl-4-piperazinyl)-ethylamino]-benzamide
2-[N-(o-Chlorobenzoyl)-2-(1-phenyl-4-piperazinyl)-ethylamino]-benzamide
2-[N-(m-Chlorobenzoyl)-2-(1-phenyl-4-piperazinyl)-ethylamino]-benzamide
2-[N-(p-Chlorobenzoyl)-2-(1-phenyl-4-piperazinyl)-ethylamino]-benzamide
2-[N-(o-Aminobenzoyl)-2-(1-phenyl-4-piperazinyl)-ethylamino]-benzamide
2-[N-(m-Aminobenzoyl)-2-(1-phenyl-4-piperazinyl)-ethylamino]-benzamide
2-[N-(p-Aminobenzoyl)-2-(1-phenyl-4-piperazinyl)-ethylamino]-benzamide
2-[N-(o-Methoxybenzoyl)-2-(1-phenyl-4-piperazinyl)-ethylamino]-benzamide
2-[N-(m-Methoxybenzoyl)-2-(1-phenyl-4-piperazinyl)-ethylamino]-benzamide
2-[N-(p-Methoxybenzoyl)-2-(1-phenyl-4-piperazinyl)-ethylamino]-benzamide
2-[N-(o-Hydroxybenzoyl)-2-[1-phenyl-4-Piperazinyl)-ethylamino]-benzamide
2-[N-(m-Hydroxybenzoyl)-2-(1-phenyl-4-piperazinyl)-ethylamino]-benzamide
2-[N-(p-Hydroxybenzoyl)-2-(1-phenyl-4-piperazinyl)-ethylamino]-benzamide
2-[N-(o-Methylbenzoyl)-2-(1-phenyl-4-piperazinyl)-ethylamino]-benzamide
2-[N-(m-Methylbenzoyl)-2-(1-phenyl-4-piperazinyl)-ethylamino]-benzamide
2-[N-(p-Methylbenzoyl)-2-(1-phenyl-4-piperzinyl)-ethylamino]-benzamide
2-[N-Benzyl-2-(1-phenyl-4-piperazinyl)-ethylamino]-benzamide
2-[N-Benzyl-1-methyl-2-(1-phenyl-4-piperazinyl)-ethylamino]-benzamide
2-[N-(o-Chlorobenzyl)-2-(1-phenyl-4-piperazinyl)-ethylamino]-benzamide
2-[N-(m-Chlorobenzyl)-2-(1-phenyl-4-piperazinyl)-ethylamino]-benzamide
2-[N-(p-Chlorobenzyl)-2-(1-phenyl-4-piperazinyl)-ethylamino]-benzamide
2-[N-(o-Aminobenzyl)-2-(1-phenyl-4-piperazinyl)-ethylamino]-benzamide
2-[N-(m-Aminobenzyl)-2-(1-phenyl-4-piperazinyl)-ethylamino]-benzamide
2-[N-(p-Aminobenzyl)-2-(1-phenyl-4-piperazinyl)-ethylamino]-benzamide
2-[N-(o-Methylbenzyl)-2-(1-phenyl-4-piperazinyl)-ethylamino]-benzamide
2-[N-(m-Methylbenzyl)-2-(1-phenyl-4-piperazinyl)-ethylamino]-benzamide
2-[N-(p-Methylbenzyl)-2-(1-phenyl-4-piperazinyl)-ethylamino]-benzamide
2-[N-(o-Methoxybenzyl)-2-(1-phenyl-4-piperazinyl)-ethylamino]-benzamide
2-[N-(m-Methoxybenzyl)-2-(1-phenyl-4-piperazinyl)-ethylamino]-benzamide
2-[N-(p-Methoxybenzyl-2-(1-phenyl-4-piperazinyl)-ethylamino]-benzamide
2-[N-(o-Hydroxybenzyl)-2-(1-phenyl-4-piperazinyl)-ethylamino]-benzamide
2-]N-(m-Hydroxybenzyl)-2-(1-phenyl-4-piperazinyl)-ethylamino]-benzamide
2-[N-(p-Hydroxybenzyl)-2-(1-phenyl-4-piperazinyl)-ethylamino]-benzamide
2-[N-Picolinoyl-2-(1-phenyl-4-piperazinyl)-ethylamino]-benzamide
2-[N-Nicotinoyl-2-(1-phenyl-4-piperazinyl)-ethylamino]-benzamide
2-[N-Isonicotinoyl-2-(1-phenyl-4-piperazinyl)-ethylamino]-benzamide
2-[N-(2-Pyridylmethyl)-2-(1-phenyl-4-piperazinyl)-ethylamino]-benzamide
2-[N-(3-Pyridylmethyl)-2-(1-phenyl-4-piperazinyl)-ethylamino]-benzamide
2-[N-(4-Pyridylmethyl)-2-(1-phenyl-4-piperazinyl)-ethylamino]-benzamide
2-[N-Acetyl-2-(1-phenyl-4-piperazinyl)-ethylamino]-benzamide
2-[N-Propionyl-2-(1-phenyl-4-piperazinyl)-ethylamino]-benzamide
2-[N-Butyryl-2-(1-phenyl-4-piperazinyl)-ethylamino]-benzamide
2-[N-Acetyl-1-methyl-2-(1-phenyl-4-piperazinyl)-ethylamino]-benzamide
2-[N-Propionyl-1-methyl-2-(1-phenyl-4-piperazinyl)-ethylamino]-benzamide
2-[N-Methyl-2-(1-phenyl-4-piperazinyl)-ethylamino]-benzamide
2-[N-Ethyl-2-(1-phenyl-4-piperazinyl)-ethylamino]-benzamide
2-[N-Propyl-2-(1-phenyl-4-piperazinyl)-ethylamino]-benzamide 2-[N-Butyl-2-(1-phenyl-4-piperazinyl)-ethylamino]-benzamide
3-Chloro-2-[3-(1-phenyl-4-piperazinyl)-propylamino]-benzamide
4-Chloro-2-[3-(1-phenyl-4-piperazinyl)-propylamino]-benzamide
5-Chloro-2-[3-(1-phenyl-4-piperazinyl)-propylamino]-benzamide
6-Chloro-2-[3-(1-phenyl-4-piperazinyl)-propylamino]-benzamide
3-Amino-2-[3-(1-phenyl-4-piperazinyl)-propylamino]-benzamide
4-Amino-2-[3-(1-phenyl-4-piperazinyl)-propylamino]-benzamide
5-Amino-2-[3-(1-phenyl-4-piperazinyl)-propylamino]-benzamide
6-Amino-2-[3-(1-phenyl-4-piperazinyl)-propylamino]-benzamide
3-Methoxy-2-[3-(1-phenyl-4-piperazinyl)-propylamino]-benzamide
4-Methoxy-2-[3-(1-phenyl-4-piperazinyl)-propylamino]-benzamide
5-Methoxy-2-[3-(1-phenyl-4-piperazinyl)-propylamino]-benzamide
6-Methoxy-2-[3-(1-phenyl-4-piperazinyl)-propylamino]-benzamide
3-Hydroxy-2-[3-(1-phenyl-4-piperazinyl)-propylamino]-benzamide
4-Hydroxy-2-[3-(1-phenyl-4-piperazinyl)-propylamino]-benzamide
5-Hydroxy-2-[3-(1-phenyl-4-piperazinyl)-propylamino]-benzamide
6-Hydroxy-2-[3-(1-phenyl-4-piperazinyl)-propylamino]-benzamide
3-Methyl-2[3-phenyl-4-piperazinyl)-propylamino]-benzamide
4-Methyl-2-[3-(1-phenyl-4-piperazinyl)-propylamino]-benzamide
5-Methyl-2-[3-(1-phenyl-4-piperazinyl)-propylamino]-benzamide
6-Methyl-2-[3-(1-phenyl-4-piperazinyl)-propylamino]-benzamide
2-[3-(1-phenyl-4-piperazinyl)-propylamino]-3-trifluoromethylbenzamide
2-[3-(1-phenyl-4-piperazinyl)-propylamino]-4-trifluoromethylbenzamide
2-[3-(1-phenyl-4-piperazinyl)-propylamino]-5-trifluoromethylbenzamide
2-[3-(1-phenyl-4-piperazinyl)-propylamino]-6-trifluoromethylbenzamide
3-Chloro-2-[1-methyl-2-(1-phenyl-4-piperazinyl)-ethylamino]-benzamide
4-Chloro-2-[1-methyl-2-(1-phenyl-4-piperazinyl)-ethylamino]-benzamide
5-Chloro-2-[1-methyl-2-(1-phenyl-4-piperazinyl)-ethylamino]-benzamide
6-Chloro-2-[1-methyl-2-(1-phenyl-4-piperazinyl)-ethylamino]-benzamide
3-Amino-2-[1-methyl-2-(1-phenyl-4-piperazinyl)-ethylamino]-benzamide
4-Amino-2-[1-methyl-2-(1-phenyl-4-piperazinyl)-ethylamino]-benzamide
5-Amino-2-[1-methyl-2-(1-phenyl-4-piperazinyl)-ethylamino]-benzamide
6-Amino-2-[1-methyl-2-(1-phenyl-4-piperazinyl)-ethylamino]-benzamide
3-Methoxy-2-[1-methyl-2-(1-phenyl-4-piperazinyl)-ethylamino]-benzamide
4-Methoxy-2-[1-methyl-2-(1-phenyl-4-piperazinyl)-ethylamino]-benzamide
5-Methoxy-2-[1-methyl-2-(1-phenyl-4-piperazinyl)-ethylamino]-benzamide
6-Methoxy-2-[1-methyl-2-(1-phenyl-4-piperazinyl)-ethylamino]-benzamide
3-Hydroxy-2-[1-methyl-2-(1-phenyl-4-piperazinyl)-ethylamino]-benzamide
4-Hydroxy-2-[1-methyl-2-(1-phenyl-4-piperazinyl)-ethylamino]-benzamide
5-Hydroxy-2-[1-methyl-2-(1-phenyl-4-piperazinyl)-ethylamino]-benzamide
6-Hydroxy-2-[1-methyl-2-(1-phenyl-4-piperazinyl)-ethylamino]-benzamide
3-Methyl-2-[1-methyl-2-(1-phenyl-4-piperazinyl)-ethylamino]-benzamide
4-Methyl-2-[1-methyl-2-(1-phenyl-4-piperazinyl)-ethylamino]-benzamide
5-Methyl-2-[1-methyl-2-(1-phenyl-4-piperazinyl)-ethylamino]-benzamide
6-Methyl-2-[1-methyl-2-(1-phenyl-4-piperazinyl)-ethylamino]-benzamide
2-[1-Methyl-2-(1-phenyl-4-piperazinyl)-ethylamino]-3-trifluoromethylbenzamide
2-[1-Methyl-2-(1-phenyl-4-piperazinyl)-ethylamino]-4-trifluoromethylbenzamide
2-[1-Methyl-2-(1-phenyl-4-piperazinyl)-ethylamino]-5-trifluoromethylbenzamide
2-[1-Methyl-2-(1-phenyl-4-piperazinyl)-ethylamino]-6-trifluoromethylbenzamide
3-Chloro-2-[2-methyl-2-(1-phenyl-4-piperazinyl)-ethylamino]-benzamide
4-Chloro-2-[2-methyl-2-(1-phenyl-4-piperazinyl)-ethylamino]-benzamide
5-Chloro-2-[2-methyl-2-methyl-2-(1-phenyl-4-piperazinyl)-ethylamino]-benzamide
6-Chloro-2-[2-methyl-2-(1-phenyl-4-piperazinyl)-ethylamino]-benzamide
3-Amino-2-[2-methyl-2-(1-phenyl-4-piperazinyl)-ethylamino]-benzamide
4-Amino-2-[2-methyl-2-(1-phenyl-4-piperazinyl)-ethylamino]-benzamide
5-Amino-2-[2-methyl-2-(1-phenyl-4-piperazinyl)-ethylamino]-benzamide
6-Amino-2-[2-methyl-2-(1-phenyl-4-piperazinyl)-ethylamino]-benzamide
3-Methoxy-2-[2-methyl-2-(1-phenyl-4-piperazinyl)-ethylamino]-benzamide
4-Methoxy-2-[2-methyl-2-(1-phenyl-4-piperazinyl)-ethylamino]-benzamide
5-Methoxy-2-[2-methyl-2-(1-phenyl-4-piperazinyl)-ethylamino]-benzamide
6-Methoxy-2-[2-methyl-2-(1-phenyl-4-piperazinyl)-ethylamino]-benzamide
3-Hydroxy-2-[2-methyl-2-(1-phenyl-4-piperazinyl)-ethylamino]-benzamide
4-Hydroxy-2-[2-methyl-2-(1-phenyl-4-piperazinyl)-ethylamino]-benzamide
5-Hydroxy-2-[2-methyl-2-(1-phenyl-4-piperazinyl)-ethylamino]-benzamide
6-Hydroxy-2-[2-methyl-2-(1-phenyl-4-piperazinyl)-ethylamino]-benzamide
3-Methyl-2-[2-methyl-2-(1-phenyl-4-piperazinyl)-ethylamino]-benzamide
4-Methyl-2-[2-methyl-2-(1-phenyl-4-piperazinyl)-ethylamino]-benzamide
5-Methyl-2-[2-methyl-2-(1-phenyl-4-piperazinyl)-ethylamino]-benzamide 6-Methyl-2-[2-methyl-2-(1-phenyl-4-piperazinyl)-ethylamino]-benzamide
2-[2-Methyl-2-(1-phenyl-4-piperazinyl)-ethylamino]-3-trifluoromethylbenzamide
2-[2-Methyl-2-(1-phenyl-4-piperazinyl)-ethylamino]-4-trifluoromethylbenzamide
2-[2-Methyl-2-(1-phenyl-4-piperazinyl)-ethylamino]-5-trifluoromethylbenzamide
2-[2-Methyl-2-(1-phenyl-4-piperazinyl)-ethylamino]-6-trifluoromethylbenzamide
1-(2-[2-(1-phenyl-4-piperazinyl)-ethylamino]-benzoyl)-piperidine
1-(3-Amino-2-[2-(1-phenyl-4-piperazinyl)-ethylamino]-benzoyl)-piperidine
1-(4-Aminio-2-[2-(1-phenyl-4-piperazinyl)-ethylamino]-benzoyl)-piperidine
1-(5-Amino-2-[2-(1-phenyl-4-piperazinyl)-ethylamino]-benzoyl)-piperidine
1-(6-Amino-2-[2-(1-phenyl-4-piperazinyl)-ethylamino]-benzoyl)-piperidine
1-(3-Methoxy-2-[2-(1-phenyl-4-piperazinyl)-ethylamaino]-benzoyl)-piperidine
1-(4-Methoxy-2-[2-(1-phenyl-4-piperazinyl)-ethylamino]-benzoyl)-piperidine
1-(5-Methoxy-2-[2-(1-phenyl-4-piperazinyl)-ethylamino]-benzoyl)-piperidine
1-(6-Methoxy-2-[2-(1-phenyl-4-piperazinyl)-ethylamino]-benzoyl)-piperidine
1-(3-Hydroxy-2-[2-(1-phenyl-4-piperazinyl)-ethylamino]-benzoyl)-piperidine
1-(4-Hydroxy-2-[2-(1-phenyl-4-piperazinyl)-ethylamino]-benzoyl)-piperidine
1-(5-Hydroxy-2-[2-(1-phenyl-4-piperazinyl)-ethylamino]-benzoyl)-piperidine
1-(6-Hydroxy-2-[2-(1-phenyl-4-piperazinyl)-ethylamino]-benzoyl)-piperidine
4-(2-[2-(1-phenyl-4-piperazinyl)-ethylamino]-benzoyl)-morpholine
4-(3-Amino-2-[2-(1-phenyl-4-piperazinyl)-ethylamino]-benzoyl)-morpholine
4-(4-Amino-2-[2-(1-phenyl-4-piperazinyl)-ethylamino]-benzoyl)-morpholine
4-(5-Amino-2-[2-(1-phenyl-4-piperazinyl)-ethylamino]-benzoyl)-morpholine
4-(6-Amino-2-[2-(1-phenyl-4-piperazinyl)-ethylamino]-benzoyl)-morpholine
4-(3-Methyoxy-2-[2-(1-phenyl-4-piperazinyl)-ethylamino]-benzoyl)-morpholine
4-(4-Methoxy-2-[2-(1-phenyl-4-piperazinyl)-ethylamino]-benzoyl)-morpholine
4-(5-Methoxy-2-[2-(1-phenyl-4-piperazinyl)-ethylamino]-benzoyl)-morpholine
4-(6-Methoxy-2-[2-(1-phenyl-4-piperazinyl)-ethylamino]-benzoyl)-morpholine
4-(3-Hydroxy-2-[2-(1-phenyl-4-piperazinyl)-ethylamino]-benzoyl)-morpholine
4-(4-Hydroxy-2-[2-(1-phenyl-4-piperazinyl)-ethylamino]-benzoyl)-morpholine
4-(5-Hydroxy-2-[2-(1-phenyl-4-piperazinyl)-ethylamino]-benzoyl)-morpholine
4-(6-Hydroxy-2-[2-(1-phenyl-4-piperazinyl)-ethylamino]-benzoyl)-morpholine
1-(2-[2-(1-Phenyl-4-piperazinyl)-ethylamino]-benzoyl)-pyrrolidine
1-(3-Amino-2-[2-(1-phenyl-4-piperazinyl)-ethylamino]-benzoyl)-pyrrolidine
1-(4-Amino-2-[2-(1-phenyl-4-piperazinyl)-ethylamino]-benzoyl)-pyrrolidine
1-(5-Amino-2-[2-(1-phenyl-4-piperazinyl)-ethylamino]-benzoyl)-pyrrolidine
1-(6-Amino-2-[2-(1-phenyl-4-piperazinyl)-ethylamino]-benzoyl)-pyrrolidine
1-(3-Hydroxy-2-[2-(1-phenyl-4-piperazinyl)-ethylamino]-benzoyl)-pyrrolidine
1-(4-Hydroxy-2-[2-(1-phenyl-4-piperazinyl)-ethylamino]-benzoyl)-pyrrolidine
1-(5-Hydroxy-2-[2-(1-phenyl-4-piperazinyl)-ethylamino]-benzoyl)-pyrrolidine
1-(6-Hydroxy-2-[2-(1-phenyl-4-piperazinyl)-ethylamino]-benzoyl)-pyrrolidine
1-(3-Methoxy-2-[2-(1-phenyl-4-piperazinyl)-ethylamino]-benzoyl)-pyrrolidine
1-(4-Methoxy-2-[2-(1-phenyl-4-piperazinyl)-ethylamino]-benzoyl)-pyrrolidine
1-(5-Methoxy-2-[2-(1-phenyl-4-piperazinyl)-ethylamino]-benzoyl)-pyrrolidine
1-(6-Methoxy-2-[2-(1-phenyl-4-piperazinyl)-ethylamino]-benzoyl)-pyrrolidine
3-Amino-N-methyl-2-[2-(1-phenyl-4-piperazinyl)-ethylamino]-benzamide
4-Amino-N-methyl-2-[2-(1-phenyl-4-piperazinyl)-ethylamino]-benzamide
5-Amino-N-methyl-2-[2-(1-phenyl-4-piperazinyl)-ethylamino]-benzamide
6-Amino-N-methyl-2-[2-(1-phenyl-4-piperazinyl)-ethylamino]-benzamide
3-Methoxy-N-methyl-2-[2-(1-phenyl-4-piperazinyl)-ethylamino]-benzamide
4-Methoxy-N-methyl-2-[2-(1-phenyl-4-piperazinyl)-ethylamino]-benzamide
5-Methoxy-N-methyl-2-[2-(1-phenyl-4-piperazinyl)-ethylamino]-benzamide
6-Methoxy-N-methyl-2-[2-(1-phenyl-4-piperazinyl)-ethylamino]-benzamide
3-Hydroxy-N-methyl-2-[2-(1-phenyl-4-piperazinyl)-ethylamino]-benzamide
4-Hydroxy-N-methyl-2-[2-(1-phenyl-4-piperazinyl)-ethylamino]-benzamide
5-Hydroxy-N-methyl-2-[2-(1-phenyl-4-piperazinyl)-ethylamino]-benzamide
6-Hydroxy-N-methyl-2-(2-(1-phenyl-4-piperazinyl)-ethylamino]-benzamide
N,N-Dimethyl-2-[2-(1-phenyl-4-(piperazinyl)-ethylamino]-benzamide
3-Amino-N,N-dimethyl-2-[2-(1-phenyl-4-piperazinyl)-ethylamino]-benzamide
4-Amino-N,N-dimethyl-2-[2-(1-phenyl-4-piperazinyl)-ethylamino]-benzamide
5-Amino-N,N-dimethyl-2-[2-(1-phenyl-4-piperazinyl)-ethylamino]-benzamide
6-Amino-N,N-dimethyl-2-[2-(1-phenyl-4-piperazinyl)-ethylamino]-benzamide
3-Methoxy-N,N-dimethyl-2-[2-(1-phenyl-4-piperazinyl)-ethylamino]-benzamide
4-Methoxy-N,N-dimethyl-2-[2-(1-phenyl-4-piperazinyl)-ethylamino]-benzamide
5-Methoxy-N,N-dimethyl-2-[2-(1-phenyl-4-piperazinyl)-ethylamino]-benzamide
6-Methoxy-N,N-dimethyl-2-[2-(1-phenyl-4-piperazinyl)-ethylamino]-benzamide
3-Hydroxy-N,N-dimethyl-2-[2-(1-phenyl-4-piperazinyl)-ethylamino]-benazmide
4-Hydroxy-N,N-dimethyl-2-[2-(1-phenyl-4-piperazinyl)-ethylamino]-benzamide
5-Hydroxy-N,N-dimethyl-2-[2-(1-phenyl-4-piperazinyl)-ethylamino]-benzamide 6-Hydroxy-N,N-dimethyl-2-[2-(1-phenyl-4-piperazinyl)-ethylamino]-benzamide
2-[1-phenyl-4-piperazinylmethylamino]-benzamide
2-[2-(1-α-Methylphenethyl-4-piperazinyl)-ethylamino]-benzamide
2-[2-(1-[o-Amino-α-methylphenyl]-4-piperazinyl)-ethylamino]-benzamide
2-[2-(1-[m-Amino-α-methylphenyl]-4-piperazinyl)-ethylamino]-benzamide
2-[2-(1-[p-Amino-α-methylphenethyl]-4-piperazinyl)-ethylamino]-benzamide
2-[2-(1-[o-Methoxy-α-methylphenethyl]-4-piperazinyl)-ethylamino]-benzamide
2-[2-(1-[m-Methoxy-α-methylphenethyl]-4-piperazinyl)-ethylamino]benzamide
2-[2-(1-[p-Methoxy-α-methylphenethyl]-4-piperazinyl)-ethylamino]-benzamide
2-[2-(1-[o-Hydroxy-α-methylphenethyl]-4-piperazinyl)-ethylamino]-benzamide
2-[2-(1-[m-Hydroxy-α-methylphenethyl]-4-piperazinyl)-ethylamino]-benzamide
2-[2-(1-[p-Hydroxy-α-methylphenethyl]-4-piperazinyl)-ethylamino]-benzamide
2-[2-(1-phenyl-4-piperazinyl)-ethylamino]-benzoic acid
Methyl 2-[2-[1-phenyl-4-piperazinyl)-ethylamino]-benzoate
3-Amino-2-[2-(1-phenyl-4-piperazinyl)-ethylamino]-benzoic acid
4-Amino-2-[2-(1-phenyl-4-piperazinyl)-ethylamino]-benzoic acid
5-Amino-2-[2-(1-phenyl-4-piperazinyl)-ethylamino]-benzoic acid
6-Amino-2-[2-(1-phenyl-4-piperazinyl)-ethylamino]-benzoic acid
Methyl 3-Amino-2-[2-(1-phenyl-4-piperazinyl)-ethylamino]-benzoate
Methyl 4-Amino-2-[2-(1-phenyl-4-piperazinyl)-ethylamino]-benzoate
Methyl 5-Amino-2-[2-(1-phenyl-4-piperazinyl)-ethylamino]-benzoate
Methyl 6-Amino-2-[2-(1-phenyl-4-piperazinyl)-ethylamino]-benzoate
3-Methoxy-2-[2-(1-phenyl-4-piperazinyl)-ethylamino]-benzoic acid
4-Methoxy-2-[2-(1-phenyl-4-piperazinyl)-ethylamino]-benzoic acid
5-Methoxy-2-[2-(1-phenyl-4-piperazinyl)-ethylamino]-benzoic acid
6-Methoxy-2-[2-(1-phenyl-4-piperazinyl)-ethylamino]-benzoic acid
Methyl 3-Methoxy-2-[2-(1-phenyl-4-piperazinyl)-ethylamino]-benzoate
Methyl 4-Methoxy-2-[2-(1-phenyl-4-piperazinyl)-ethylamino]-benzoate
Methyl 5-Methoxy-2-[2-(1-phenyl-4-piperazinyl)-ethylamino]-benzoate
Methyl 6-Methoxy-2-[2-(1-phenyl-4-piperazinyl)-ethylamino]-benzoate
3-Hydroxy-2-[2-(1-phenyl-4-piperazinyl)-ethylamino]-benzoic acid
4-Hydroxy-2-[2-(1-phenyl-4-piperazinyl)-ethylamino]-benzoic acid
5-Hydroxy-2-[2-(1-phenyl-4-piperazinyl)-ethylamino]-benzoic acid
6-Hydroxy-2-[2-(1-phenyl-4-piperazinyl)-ethylamino]-benzoic acid
Methyl 3-Hydroxy-2-[2-(1-phenyl-4-piperazinyl)-ethylamino]-benzoate
Methyl 4-Hydroxy-2-[2-(1-phenyl-4-piperazinyl)-ethylamino]-benzoate
Methy 5-Hydroxy-2-[2-(1-phenyl-4-piperazinyl)-ethylamino]-benzoate
Methyl 6-Hydroxy-2-[2-(1-phenyl-4-piperazinyl)-ethylamino]-benzoate
Methyl 2-[1-Methyl-2-(1-phenyl-4-piperazinyl)-ethylamino]-benzoate
Methyl 3-Amino-2-[1-methyl-2-(1-phenyl-4-piperazinyl(-ethylamino]-benzoate
Methyl 4-Amino-2-[1-methyl-2-(1-phenyl-4-piperazinyl)-ethylamino]-benzoate
Methyl 5-Amino-2-[1-methyl-2-(1-phenyl-4-piperazinyl)-ethylamino]-benzoate
Methyl 6-Amino-2-[1-methyl-2-(1-phenyl-4-piperazinyl)-ethylamino]-benzoate
Methy 3-Methoxy-2-[1-methyl-2-(1-phenyl-4-piperazinyl)-ethylamino]-benzoate
Methyl 4-Methoxy-2-[1-methyl-2-(1-phenyl-4-piperazinyl)-ethylamino]-benzoate
Methyl 5-Methoxy-2-[1-methyl-2-(1-phenyl-4-piperazinyl)-ethylamino]-benzoate
Methyl 6-Methoxy-2-[1-methyl-2-(1-phenyl-4-piperazinyl)-ethylamino]-benzoate
Methyl 3-Hydroxy-2-(1-methyl-2-(1-phenyl-4-piperazinyl)-ethylamino]-benzoate
Methyl 4-Hydroxy-2-(1-methyl-2-(1-phenyl-4-piperazinyl)-ethylamino]-benzoate
Methyl 5-Hydroxy-2-(1-methyl-2-(1-phenyl-4-piperazinyl)-ethylamino]-benzoate
Methyl 6-Hydroxy-2-(1-methyl-2-(1-phenyl-4-piperazinyl)-ethylamino]-benzoate
Methyl 2-[N-Benzoyl-2-(1-phenyl-4-piperazinyl)-ethylamino]-benzoate
Methyl 3-Amino-2-[N-benzoyl-2-(1-phenyl-4-piperazinyl)-ethylamino]-benzoate
Methyl 4-Amino-2-[N-benzoyl-2-(1-phenyl-4-piperazinyl)-ethylamino]-benzoate
Methyl 5-Amino-2-[N-benzoyl-2-(1-phenyl-4-piperazinyl)-ethylamino]-benzoate
Methyl 6-Amino-2-[N-benzoyl-2-(1-phenyl-4-piperazinyl)-ethylamino]-benzoate
Methyl 3-Methoxy-2-[N-benzoyl-2-(1-phenyl-4-piperazinyl)-ethylamino]-benzoate
Methyl 4-Methoxy-2-[N-benzoyl-2-(1-phenyl-4-piperazinyl)-ethylamino]-benzoate
Methyl 5-Methoxy-2-[N-benzoyl-2-(1-phenyl-4-piperazinyl)-ethylamino]-benzoate
Methyl 6-Methoxy-2-[N-benzoyl-2-(1-phenyl-4-piperazinyl)-ethylamino]-benzoate
Methyl 3-Hydroxy-2-[N-benzoyl-2-(1-phenyl-4-piperazinyl)-ethylamino]-benzoate
Methyl 4-Hydroxy-2-[N-benzoyl-2-(1-phenyl-4-piperazinyl)-ethylamino]-benzoate
Methyl 5-Hydroxy-2-[N-benzoyl-2-(1phenyl-4-piperazinyl)-ethylamino]-benzoate
Methyl6-Hydroxy-2-[N-benzoyl-2-[N-benzoyl-2-(1-phenyl-4-piperazinyl)-ethylamino]-benzoate
Methyl 2-[N-Benzyl-2-(1-phenyl-4-piperazinyl)-ethylamino]-benzoate
Methyl 3-Amino-2-[N-benzyl-2-(1-phenyl-4-piperazinyl)-ethylamino]-benzoate
Methyl 4-Amino-2-[N-benzyl-2-(1-phenyl-4-piperazinyl)-ethylamino]-benzoate
Methyl 5-Amino-2-[N-benzyl-2-(1-phenyl-4-piperazinyl)-ethylamino]-benzoate
Methyl 6-Amino-2-[N-benzyl-2-(1-phenyl-4-piperazinyl)-ethylamino]-benzoate Methyl 3-Methoxy-2-[N-benzyl-2-(1-phenyl-4-piperazinyl)-ethylamino]-benzoate
Methyl 4-Methoxy-2-[N-benzyl-2-(1-phenyl-4-piperazinyl)-ethylamino]-benzoate
Methyl 5-Methoxy-2-[N-benzyl-2-(1-phenyl-4-piperazinyl)-ethylamino]-benzoate
Methyl 6-Methoxy-2-[N-benzyl-2-(1-phenyl-4-piperazinyl)-ethylamino]-benzoate
Methyl 3-Hydroxy-2-[N-benzyl-2-(1-phenyl-4-piperazinyl)-ethylamino]-benzoate
Methyl 4-Hydroxy-2-[N-benzyl-2-(1-phenyl-4-piperazinyl)-ethylamino]-benzoate
Methyl 5-Hydroxy-2-[N-benzyl-2-(1phenyl-4-piperazinyl)-ethylamino]-benzoate
Methyl 6-Hydroxy-2-[N-benzyl-2-(1-phenyl-4-piperazinyl)-ethylamino]-benzoate
Methyl 2-[N-Picolinoyl-2-(1-phenyl-4-piperazinyl)-ethylamino]-benzoate
Methyl 3-Amino-2-[N-picolinoyl-2-(1-phenyl-4-piperazinyl)-ethylamino]-benzoate
Methyl 4-Amino-2-[N-picolinoyl-2-(1-phenyl-4-piperazinyl)-ethylamino]-benzoate
Methyl 5-Amino-2-[N-picolinoyl-2-(1-phenyl-4piperazinyl)-ethylamino]-benzoate
Methyl 6-Amino-2-[N-picolinoyl-2-(1-phenyl-4-piperazinyl)-ethylamino]-benzoate
Methyl 3-Methoxy-2-[N-picolinoyl-2-(1-phenyl-4-piperazinyl)-ethylamino]-benzoate
Methyl 4-Methoxy-2-[N-picolinoyl-2-(1-phenyl-4-piperazinyl)-ethylamino]-benzoate.
Methyl 5-Methoxy-2-[N-picolinoyl-2-(1-phenyl-4-piperazinyl)-ethylamino]-benzoate
Methyl 6-Methoxy-2-[N-picolinoyl-2-(1-phenyl-4-piperazinyl)-ethylamino]-benzoate
Methyl 3-Hydroxy-2-[N-picolinoyl-2-(1-phenyl-4-piperazinyl)-ethylamino]-benzoate
Methyl 4-Hydroxy-2-[N-picolinoyl-2-(1-phenyl-4-piperazinyl)-ethylamino]-benzoate
Methyl 5-Hydroxy-2-[N-picolinoyl-2-(1-phenyl-4-piperazinyl)-ethylamino]-benzoate
Methyl 6-Hydroxy-2-[N-picolinoyl-2-(1-phenyl-4-piperazinyl)-ethylamino]-benzoate
Methyl 2-[N-(2-Pyridylmethyl)-2-(1-phenyl-4-piperazinyl)-ethylamino]-benzoate
Methyl 3-Amino-2-[N-(2-pyridylmethyl)-2-(1-phenyl-4-piperazinyl)-ethylamino]-benzoate
Methyl 4-Amino-2-[N-(2-pyridylmethyl)-2-(1-phenyl-4-piperazinyl)-ethylamino]-benzoate
Methyl 5-Amino-2-[N-(2-pyridylmethyl)-2-(1-phenyl-4-piperazinyl)ethylamino]-benzoate
Methyl 6-Amino-2-[N-(2-pyridylmethyl)-2-(1-phenyl-4-piperazinyl)-ethylamino]-benzoate
Methyl 3-Methoxy-2-[N-(2-pyridylmethyl)-2-(1-phenyl-4-piperazinyl)-ethylamino]-benzoate
Methyl 4-Methoxy-2-[N-(2-pyridylmethyl)-2-(1-phenyl-4-piperazinyl)-ethylamino]-benzoate
Methyl 5-Methoxy-2-[N-(2-pyridylmethyl)-2-(1-phenyl-4-piperazinyl)-ethylamino]-benzoate
Methyl 6-Methoxy-2-[N-(2-pyridylmethyl)-2-(1-phenyl-4-piperazinyl)-ethylamino]-benzoate
Methyl 3-Hydroxy-2-[N-(2-pyridylmethyl)-2-(1-phenyl-4-piperazinyl)-ethylamino]-benzoate
Methyl 4-Hydroxy-2-[N-(2-pyridylmethyl)-2-(1-phenyl-4-piperazinyl)-ethylamino]-benzoate
Methyl 5-Hydroxy-2-[N-(2-pyridylmethyl)-2-(1-phenyl-4-piperazinyl)-ethylamino]-benzoate
Methyl 6-Hydroxy-2-[N-(2-pyridylmethyl)-2-(1-phenyl-4-piperazinyl)-ethylamino]-benzoate
2-(1-Phenyl-4-piperazinylmethylamino)-benzoic acid
Methyl 2-(1-phenyl-4-piperazinylmethylamino)-benzoate
N-Benzyl-N-2-(1-phenyl-4-piperazinyl)-ethyl-o-aminophenyl-propionate
N-Benzyl-N-[1-methyl-2-(1-phenyl-4-piperazinyl)]-ethyl-o-aminophenyl propionate
N-Phenyl-N-2-(1-phenyl-4-piperazinyl)-ethyl-o-aminophenyl-propionate
N-Phenyl-N-[1-methyl-2-(1-methyl-4-piperazinyl)]-ethyl-o-aminophenylpropionate Additional examples of compounds of Group A are as follows:

6-Hydroxy-1-[1-methyl-2-(1-phenyl-4-piperazinyl)-ethyl]-2phenyl-1,2,3,4-tetrahydro-4-quinazolinone
6-Methoxy-1-[1-methyl-2-(1-phenyl-4-piperazinyl)-ethyl]-2-phenyl-1, 1,2,3,4-tetrahydro-4-quinazolinone
1-[2-(4-Morpholinyl)-ethyl]-2-phenyl-1,2,3,4-tetrahydro-4-quinazolinone
6-Amino-1-[2(4-morpholinyl)-ethyl]-2-phenyl-1,2,3,4-tetrahydro-4-quinazolinone
2-Phenyl-1-[2-(4-thiomorpholinyl)-ethyl]-1,2,3,4-tetrahydro-4-quinazolinone
6-Amino-2-phenyl-1-[2(4-thiomorpholinyl)-ethyl]-1,2,3,4-tetrahydro-4-quinazolinone
2-Phenyl-1-[2-(1-piperidinyl)-ethyl]-1,2,3,4-tetrahydro-4-quinazolinone
1-[2-(4-phenyl-1-piperidinyl)-ethyl]-2-phenyl-1,2,3,4-tetrahydro-4-quinazolinone
3-Methyl-1-[2-(4-phenol-1-piperidinyl)-ethyl]-2-phenyl-1,2,3,4-tetrahydro-4-quinazolinone
1-[1-Methyl-2-(4-phenyl-1-piperidinyl)-ethyl]-2-phenyl-1,2,3,4-tegrahydro-4-quinazolinone
6-Amino-1-[2-(4-phenyl-1-piperidinyl)-ethyl]-2-phenyl-1,2,3,4-tetrahydro-4-quinazolinone
6-Hydroxy-1-[2-(4-phenyl-1-piperidinyl)-ethyl]-2-phenyl-1,2,3,4-tetrahydro-4-quinazolinone
6-Methoxy-1-[2-(4-phenyl-1-piperidinyl)-ethyl]-2-phenyl-1,2,3,4-tetrahydro-4-quinazolinone
2-Methyl-1-[2-phenyl-1-piperidinyl)-ethyl]-1,2,3,4-tetrahydro-4-quinazolinone
6-Amino-2-methyl-1-[2-(4-phenyl-1-piperidinyl)-ethyl]-1,2,3,4-tetrahydro-4-quinazolinone
2-(p-Hydroxyphenyl)-1-[2-(4-phenyl-1-piperidinyl)-ethyl]-1,2,3,4-tetrahydro-4-quinazolinone
6Amino-2-(p-Hydroxyphenyl)-1-[2-(4-phenyl-1-piperidinyl)-ethyl]-1,2,3,4-quinazolinone
2-(p-Methoxyphenyl)-1-[2-(4-phenyl-1-piperdinyl)-ethyl]-1,2,3,4-tetrahydro-4-quinazolinone
6-Amino-2-(p-Methoxyphenyl)-1-[2-(4-phenyl-1-piperidinyl)-ethyl]-1,2,3,4-tetrahydro-4-quinazolinone
2-(p-Aminophenyl)-1-[2(4-phenyl-1-piperidinyl)-ethyl]-1,2,3,4-tetrahydro-4-quinazolinone
6 -Amino-2-p-Aminophenyl)-1-[2-(4-phenyl-1-piperidinyl)-ethyl]-1,2,3,4-tetrahydro-4-quinazolinone
2,2-Dimethyl-1-[2-(4-phenyl-1-piperidinyl)-ethyl]-1,2,3,4-tetrahydro-4-quinazolinone
1'-[2(4-Phenyl-1-piperidinyl)-ethyl]-spiro(cyclobutane-1,2'(1'H)-quinazolin]-4'(3'H)-one
1'-[2-(4-Phenyl-1-piperidinyl)-ethyl]-spiro (cyclopentane-1,2'(1'H)-quinazolin]-4'(3'H) -one
1-[2-(4-Methyl-1-piperidinyl)-ethyl]-2-phenyl-1,2,3,4-tetrahydro-4-quinazolinone 3-Methyl-1-[2-(4-methyl-1-piperidinyl)-ethyl]-2-phenyl-1,2,3,4-tetrahydro-4-quinazolinone
1-[1-Methyl-2-methyl-1-piperidinyl)-ethyl]-2-phenyl-1,2,3,4-tetrahydro-4-quinazolinone
6-Amino-1-[2-(4-methyl-1-piperidinyl)-ethyl]-2-phenyl-1,2,3,4-tetrahydro-4-quinazolinone
6-Hydroxy-1-[2-(4-methyl-1-piperidinyl)-ethyl]-2-phenyl-1,2,3,4-tetrahydro-4-quinazolinone
6-Methoxy-1-[2-(4-methyl-1-piperidinyl)-ethyl]-2-phenyl-1,2,3,4-tetrahydro-4-quinazolinone
2-Methyl-1-[2-(4-methyl-1-piperidinyl)-ethyl]-1,2,3,4-tetrahydro-4-quinazolinone
6-Amino-2-methyl-1-[2-(4-methyl-1-piperidinyl)-ethyl]-1,2,3,4-tetrahydro-4-quinazoline
2-(p-Hydroxyphenyl)-1-[2-(4-methyl-1-piperidinyl)-ethyl]-1,2,3,4-tetrahydro-4-quinazolinone
6-Amino-2-(p-Hydroxyphenyl)-1-[2-(4-methyl-1-piperidinyl)-ethyl]-1,2,3,4-tetrahydro-4-quinazolinone
2-(p-Methoxyphenyl)-1-[2-(4-methyl-1-piperidinyl)-ethyl]-1,2,3,4-tetrahydro-4-quinazolinone
6-Amino-2-(p-Methoxyphenyl)-1-[2-(4-methyl-1-piperidinyl)-ethyl]-1,2,3,4-tetrahydro-4-quinazolinone
2-(p-Aminophenyl)-1-[2, -(4-methyl-1-piperidinyl)-ethyl]-1,2,3,4-tetrahydro-4-quinazolinone
6-Amino-2-(p-Aminophenyl)-1-[2-(4-methyl-1-piperidinyl)-ethyl]-1,2,3,4-tetrahydro-4-quinazolinone
2,2-Dimethyl-1-[2-(4-methyl-1-piperidinyl)-ethyl]-1,2,3,4-tetrahydro-4-quinazolinone
1'-[2-(4-Methyl-1-piperidinyl)-ethyl]-spiro (cyclobutane-1,2'(1'H)-quinazolin)-4'(3'H)-one
1'-[2-(4-Methyl-1-piperidinyl)-ethyl]-spiro (cyclopentane-1,2'(1'H)-quinazolin)-4'(3'H)-one
1-[2-(4-Hydroxy-4-phenyl-1-piperidinyl)-ethyl]-2-phenyl-1,2,3,4-tetrahydro-4-quinazolinone
1-[2-(4-Acetoxy-4-phenyl-1-piperidinyl)-ethyl]-2-phenyl-1,2,3,4-tetrahydro-4-quinazoline
1-[2-(4-Phenyl-4-propoxy-1-piperidinyl)-ethyl]-2-phenyl-1,2,3,4-tetrahydro-4-quinazolinone
1-[2-(4-Butoxy-4-phenyl-1-piperidinyl)-ethyl]-2-phenyl-1,2,3,4-tetrahydro-4-quinazolinone
1-[2-(4-Isobutoxy-4-phenyl-1-pipridinyl)-ethyl]-2-phenyl-1,2,3,4-tetrahydro-4-quinazolinone
6-Hydroxy-1-[2-(4-hydroxy-4-phenyl-1-piperidinyl)-ethyl]-2-phenyl-1,2,3,4-tetrahydro-4-quinazolinone
6-Amino-1-[2-(4-hydroxy-4-phenyl-1piperidinyl)-ethyl]-2-phenyl-1,2,3,4-tetrahydro-4-quinazolinone
6-Methoxy-1-[2-(4-hydroxy-4-phenyl-1-piperidinyl)-ethyl]-2-phenyl-1,2,3,4-tetrahydro-4-quinazolinone
2-(p-Hydroxyphenyl)-1-[2-hydroxy-4-phenyl-1-piperidinyl)-ethyl]-1,2,3,4-tetrahydro-4-quinazolinone
1-[2-(4-Hydroxy-4-phenyl-1-piperidinyl)-ethyl]-2-(p-methoxy-phenyl)-1,2,3,4-tetrahydro-4-quinazolinone
2-(p-Aminophenyl)-1-[2-(4-hydroxy-4phenyl-1-piperidinyl)-ethyl]-1,2,3,4-tetrahydro-4-quinazolinone
6-Amino-1-[2-(4-acetoxy-4-phenyl-1-piperidinyl)-ethyl]-2-phenyl-1,2,3,4-tetrahydro-4-quinazolinone
6Amino-1-[2-(4-propoxy-4-phenyl-1-piperidinyl)-ethyl]-2-phenyl-1,2,3,4-tetrahydro-4-quinazolinone
6-Amino-1-[2-butoxy-4-phenyl-1piperidinyl)-ethyl]-2-phenyl-1,2,3,4-tetrahydro-4-quinazolinone
2-(p-Aminophenyl)-1-[2-(4-acetoxy-4-phenyl-1-piperidinyl)-ethyl]-1,2,3,4-tetrahydro-4-quinazolinone
2-(p-Aminophenyl)-1-[2-(4-propoxy-4-phenyl-1-piperidinyl)-ethyl]-1,2,3,4-tetrahydro-4-quinazolinone
2-(p-Aminophenyl)-1-[2-(4-butoxy-4-phenyl-1piperidinyl)-ethyl-1,2,3,4-tetrahydro-4-quinazolinone
6-Methoxy-1-[2-(4-propoxy-4phenyl-1-piperidinyl)-ethyl]-2-phenyl-1,2,3,4-quinazolinone
6-Hydroxy-1-[2-(4-propoxy-4-phenyl-1-piperidinyl)-ethyl]-2-phenyl-1,2,3,4-tetrahydro-4-quinazolinone
1-[2-(4-Acetoxy-4-phenyl-1piperidinyl)-1-methyl-ethyl]-2-phenyl-1,2,3,4-tetrahydro-4-quinazolinone
1-[1-Methyl-2-(4-propoxy-4-phenyl-1piperidinyl)-ethyl]-2-phenyl-1,2,3,4-tetrahydro-4-quinazolinone
2-(p-Aminophenyl)-1-[1-methyl-2-(4-propoxy-4-phenyl-1-piperidinyl)-ethyl]-1,2,3,4-tetrahydro-4-quinazolinone
6-Amino-1-[1-methyl-2-(4-propoxy-4-phenyl-1-piperidinyl)-ethyl]-2-phenyl-1,2,3,4-tetrahydro-4-quinazolinone
6-Hydroxy-1-['1-methyl-2-(4-propoxy-4-phenyl-1-piperidinyl)-ethyl]-2-phenyl-1,2,3,4-tetrahydro-4-quinazolinone
6-Methoxy-1-[1-methyl-2-(4-Propoxy-4-phenyl-1-piperidinyl)-ethyl]-2-phenyl-1,2,3,4-tetrahydro-4-quinazolinone
1-[2-(1-[1-Methyl-2-phenethyl]-4-piperidinyl)-ethyl]-2-phenyl-1,2,3,4-tetrahydro-4-quinazolinone
1-[2-(1-Methyl-2-phenethyl]-4-piperazinyl)-ethyl]-2-methyl-1,2,3,4-tetrahydro-4-quinazolinone
2-Benzyl-2-methyl-1-[2-(1-phenyl-4-piperazinyl)-ethyl]-1,2,3,4-tetrahydro-4-quinazolinone Additional examples of compounds of Group B are as follows:

2-[2-(4-Morpholinyl)-ethylamino]-benzamide
5-Amino-2-[2-(4-morpholinyl)-ethylamino]-benzamide
2-[2-(4-Thiomorpholinyl)-ethylamino]-benzamide
5-Amino-2-[2-(4-thiomorpholinyl)-ethylamino]-benzamide
2-[2-(1-Piperidinyl)-ethylamino]-benzamide
2-[2-(4-Phenyl-1-piperidinyl)-ethylamino]-benzamide
N-Methyl-2-[2-(4-phenyl-1-piperidinyl)-ethylamino]-benazamide
2-[1-Methyl-2-(4-phenyl-1-piperidinyl)-ethylamino]-benzamide
5-Amino-2-[2-[2-(4-phenyl-1-piperidinyl)-ethylamino]-benzamide
5-Hydroxy-2-[2-(4-phenyl-1-piperidinyl)-ethylamino]-benzamide
5-Methoxy-2-[2-(4-phenyl-1-piperidinyl)-ethylamino]-benzamide
2-[2-(4-Methyl-1-piperdinyl)-ethylamino]-benzamide
N-Methyl-2-2-(4-methyl-1-piperidinyl)-ethylamino]-benzamide
2-[1-Methyl-2-(4-methyl-1-piperidinyl)-ethylamino]-benzamide
5-Amino-2-[2-(4-methyl-1-piperidinyl)-ethylamino]-benzamide
5-Hydroxy-2-[2-(4 -methyl-1-piperidinyl)-ethylamino]-benzamide
5-Methoxy-2-[2-(4-methyl-1-piperidinyl)-ethylamino]-benzamide
2-[2-(4-Hydroxy-4-phenyl-1-piperidinyl)-ethylamino]-benzamide
2-[2-(4-Acetoxy-4-phenyl-1-piperidinyl)-ethylamino]-benzamide 2-[2-(4-Phenyl-4propoxy-1-piperidinyl)-ethylamino]-benzamide
2-[2-(4-Butoxy-4-phenyl-1-piperidinyl)-ethylamino]-benzamide
2-[2-(4-Isobutoxy-4-phenyl-1-piperidinyl)-ethylamino]-benzamide
5-Hydroxy-2-[2-(4-hydroxy-4-phenyl-1-piperidinyl)-ethylamino]-benzamide
5-Amino-2-[2-(4-hydroxy-4-phenyl-1-piperidinyl)-ethylamino]-benzamide
2-[2-(4-Hydroxy-4-phenyl-1-piperidinyl)-ethylamino]-5-methoxy-benzamide
5-Amino-2-[2-(4-acetoxy-4-phenyl-1-piperidinyl)-ethylamino]-benzamide
5-Amino-2-[2-(4-phenyl-4-propoxy-1-piperidinyl)-ethylamino]-benzamide
5-Amino-2-[2-(4-butoxy-4-phenyl-1-piperidinyl)-ethylamino]-benzamide
5-Methoxy-2-[2-(4-phenyl-4-propoxy-1-piperidinyl)-ethylamino]-benzamide
5-Hydroxy-2-[2-(4-phenyl-4-propoxy-1-piperidinyl)-ethylamino]-benzamide
2-[2-(4-Acetoxy-4-phenyl-1-piperidinyl)-1-methyl-ethylamino]-benzamide
2-[1-Methyl-2-(4-phenyl-4-propoxy-1-piperidinyl)-ethylamino]-benzamide
5-Amino-2-[1-methyl-2-(4-phenyl-4-propoxy-1-piperidinyl)-ethylamino]-benzamide
5-Methoxy-2-[1-methyl-2-(4-phenyl-4-propoxy-1-piperidinyl)-ethylamino]-benzamide
5-Hydroxy-2-[1-methyl-2-(4-phenyl-4-propoxy-1-piperidinyl)-ethylamino]-benzamide
2-[2-(1-[1-Methyl-2-phenethyl]-4-piperazinyl)-ethylamino]-benzamide If desired the above described compounds may be transformed into their acid addition salts, or quanternary ammonium salts by customary methods. For instance the acid addition salts may be obtained by dissolving the free base in a suitable solvent and acidifying the solution with the desired acid. Suitable pharmacologically effective acid addition salts include the sulfates, hydrochlorides, phosphates, cyclohexyl sulfamates, maleates, citrates, tartrates, succinates, ethane disulfomates, methane, sulfonates, isethionates, and the resinates obtained by reacting the amine group of the compound with a cation exchange resin such as a sulfonic, carboxylic, or phosphoric acid cation exchange resin.

To prepare a quaternary ammonium salt the free base is merely reacted with a suitable quaternerizing agent, such as an alkyl halide, an aralkyl halide or dialkyl sulfate, preferably in the presence of an inert organic acid.

The following working examples further illustrate the invention.

EXAMPLE I

Preparation of 2-[2-(4-[1-Phenyl]piperazinyl)ethylamino]-benzamide (730-372)

| | 1-Phenyl-4-(2-hydroxyethyl)piperazine | |
|---|---|---|
| Step 1: | N-Phenylpiperazine | 519 gms. |
| | Ethylene oxide | 179 gms. |
| | Methanol (absolute) | 800 ml. |

Charged phenylpiperazine and methanol, cooled to 0 to −10° and added the ethylene oxide over 1½ hours. (Rate of addition is not important.) Removed cooling bath and allowed temperature to rise to 40°, cooling to keep below 40° until temperature stops rising. Heated at 65° for 1½ hours, and added the methanol solution to hot heptane (gradually.) Methanol was azeotroped out, adding heptane to keep the volume at 10 liters. Decanted from the insoluble oil and cooled to room temperature to give 336 gms., m.p. 79°–80.5°, plus a hard mass which apparently resulted from initial oiling out and then crystallization of the oil. This was extracted with hot heptane to give another 119 gms. of product. Yield = 69%.

| | 1-Phenyl-4-(2-hydroxyethyl)piperazine hydrochloride | |
|---|---|---|
| Step 2: | 1-Phenyl-4-(2-hydroxyethyl)piperazine | 335 gms. |
| | Methanol (anhydrous) | 1075 ml. |

HCL gas was bubbled into a solution of the 1-Phenyl-4-(2-hydroxyethyl) piperazine in methanol until the mixture was acidic, cooling to keep the temperature below 30°. The solid was filtered, washed with methanol and air dried to give 202 gms., m.p. 151°–155°. The mother liquor was used to dissolve 119 gms. of 1-Phenyl-4-(2-hydroxyethyl)piperazine and the solution acidified as above to give 179 gms., m.p. 153°–186°. Concentration of the mother liquor gave 116 gms., crop 2, m.p. 150°–152°. Yield = 92.7%.

| | 1-Phenyl-4-(2-chloroethyl)piperazine dihydrochloride | |
|---|---|---|
| | 1-Phenyl-4-(2-hydroxyethyl)piperazine HCL | 200 gms. |
| Step 3: | Chloroform | 1450 ml. |
| | Thionyl chloride | 110 ml. |

The HCL salt was suspended in chloroform and thionyl chloride added over 1½ hours. The reaction mixture was refluxed 6 hours, cooled to room temperature, filtered and washed solid with chloroform. The air dried product was recrystallized from 2.5 liters methanol to give 214 gms., m.p. 215°–218°. Yield = 87%

| | 2-[2-(4-[1-Phenyl]piperazinyl)ethylamino]benzamide | |
|---|---|---|
| Step 4: | o-Aminobenzamide | 3260 gms. |
| | 1-Phenyl-4-(2-chloroethyl)piperazine dihydrochloride | 6500 gms. |
| | Triethylamine | 7070 gms. |
| | Diglyme | 75 L. |

The reaction was run in 10 portions. The above materials were heated at 150° for 24 hours, cooled to room temperature and the solid filtered and washed with diglyme. The filtrate was evaporated to dryness on the rotovap at about 70° C. The diglyme residue was stirred with 2L. isopropanol and the solid filtered and washed with isopropanol, then with ether. Combined solids were recrystallized from 40L. of about 80% EtOH −20% water to give 1561 gm., m.p. 161.5°–2.5°. Concentration of the filtrate to 10 L. gave a second crop of 587 gms. which was recrystallized to give 477 gms., m.p. 161.5°–2.3°.

EXAMPLE II

Preparation of
1-[2-(1-Phenyl-4-piperazinyl)ethyl[-2-phenyl-1,2,3,4-tetrahydro-4-quinazolinone (740-222)

| Step 1: | 2-[2-(4-[1-Phenyl] piperazinyl)ethylamino]benzamide | 1000 gms. |
|---|---|---|
| | Benzaldehyde | 342 gms. |
| | Piperidine | 148 gms. |
| | Ethanol | 9 L. |

Charged all starting materials and refluxed 24 hours. The reaction was run in 2 parts and the reaction mixtures combined, seeded and cooled to room temperature overnight. The solid was filtered and washed to give 960 gms. crude. The crude product was recrystallized from 7.2 L. benzene and the product was dried at 95°–120° and 2 mm pressure for 10 hours to give 550 gm., m.p. 142.5°–3.5°. Concentration of the benzene mother liquor gave a second crop of 235 gm. (before drying under vacuum).

EXAMPLE III

Preparation of
1-[2-(1-Phenyl-4piperazinyl)-ethyl]-2-phenyl-4[1H]-quinazolinone hydrochloride To a solution of 16.2 gm. (0.05 M) of the substituted benzamide (III, prepared as in Example I, Step 4) in 200 ml. of pyridine, 7.73 ml. (0.055M) of benzoyl chloride was added dropwise at 15°. The solution was refluxed for 2 hours and cooled to room temperature, and the solid formed was filtered off. It was recrystallized from 275 ml. of hot water to yield 10 gm. (44%) of white solid melting at 260°–262° C.

Preparation of
1-[2-(1-Phenyl-4-piperazinyl)-ethyl[-2-phenyl-1,2,3,4-tetrahydro-4-quinazolinone The free base of the above material was liberated, and 2.5 gm. (0.0061M) of this and 0.3 gm. (0.0022M) of aluminum chloride were put into 120 ml. of diglyme. To this was added 0.29 gm. (0.0076 M) of sodium borohydride in 30 ml. of diglyme, dropwise over 15 minutes at room temperature.

The temperature was brought to 85° and kept there for 1 hour, and then the solution was cooled to 20° in an icebath and 20 ml. of water was added along with enough hydrochloric acid to bring the pH to 5.

The clear solution was taken down on the rotovap to give a yellow solid, which was triturated with cold water and filtered to give 3.2 gm. of white solid, melting at 268°–270° (decomp.).

1.0 gm. of the solid was freed from its salt form and recrystallized from 10 ml. of benzene to yield, after drying overnight at 95°, 0.25 gm. of white solid, melting at 142°–143° C. A mixed melting point with an authentic sample of 740-222 showed no depression.

EXAMPLE IV

| 2-[2-(4-[1-Phenyl] piperazinyl) ethylamino] benzamide cyclohexyl sulfamate | |
|---|---|
| 2-[2-(4-[1-Phenyl] piperazinyl) ethylamino] benzamide | 15.2 gms. |
| Cyclohexylsulfamic acid | 9.0 gms. |
| Tetrahydrofuran | 300 . ml. |

The benzamide was dissolved in about 250 ml. tetrahydrofuran and a solution of cyclohexylsulfamic acid in about 50 ml. tetrahydrofuran was added. The solid which precipitated was filtered, washed, and dried and then recrystallized from a mixture of 600 ml. isopropanol, 100 ml. methanol, and 10 drops of 10% NaOH to give 13 gms., m.p. 152°–4°.

EXAMPLE V

Preparation of 2-[2-(4-[1-Phenyl]piperazinyl)ethylamino]benzamide phosphate

| 2-[2-(4-1-Phenyl] piperazinyl) ethylamino] benzamide | 90 gm.s |
|---|---|
| Phosphoric acid (85%) | 45 ml. |
| Ethanol (95) | 450 ml. |

The benzamide was suspended in ethanol and a mixture was 45 ml. phosphoric acid in 225 ml. was added. The mixture was stirred, heated to solution, filtered, and left overnight. The solid product was filtered, washed with ethanol, dried, and recrystallized from 450 ethanol and 240 ml. water to give 64 gms., m.p. 185°–6.5°.

EXAMPLE VI

Preparation of 2-[2-(4-[1-Phenyl]piperazinyl)ethylamino]benzamide hydrochloride

| 2-[2-(4-[1-Phenyl] piperazinyl) ethylamino] benzamide | 250 gms. |
|---|---|
| Ethanol 95% | 4 l. |
| HCl concentrated | 71 ml. |

A solution of 71 ml. concentrated HCL in 213 ml. water was added to a hot solution of the benzamide in 4 l. of ethanol. The solution was cooled to 30° and the solid filtered, washed with alcohol, and dried over $P_2O_5$ under vacuum to give 249 gms., m.p. 257.5°–60° (dec.).

EXAMPLE VII

Preparation of 2-[-(1-[p-Methoxyphenyl]-4-piperazinyl)ethylamino] benzamide (751-295)

| 1-(p-Methoxyphenyl)-4-(2-hydroxyethyl) piperazine hydrochloride | | |
|---|---|---|
| Step 1: | 1-(p-Methoxyphenyl) piperazine | 26.5 gms. |
| | Methanol (absolute) | 100. ml. |
| | Ethylene oxide | 7.35 gms. |

1-(p-Methoxyphenyl) piperazine was dissolved in methanol and ethylene oxide added at −20°. The mixture was stirred while warming up to room temperature (1 hour), 2½ hours at room temperature, and 1 hour at 35°. An additional 1 ml. ethylene oxide was added, the mixture was stirred 1 hour at 50° and cooled. To the reaction mixture was added 75 ml. of a solution of HCl in methanol containing 10 gms. HCl in 100 ml. Ether (200 ml.) was added and the solid filtered after 1 hour to give 30 gms. product which was used without further purification.

| 1-(p-Methoxyphenyl)-4-(2-chloroethyl) piperazine dihydrochloride | |
|---|---|
| Step 2* | 1-(p-Methoxyphenyl)-4-(2-hydroxyethyl) piperazine hydrochloride | 30 gms. |
| | Chloroform | 500 ml. |
| | Thionyl chloride | 33 gms. |

The HCl salt was suspended in chloroform and thionyl chloride added dropwise, at room temperature, over 1hour. The reaction mixture was refluxed 8 hours, stirred 12 hours at room temperature. The solid was filtered and recrystallized from 180 ml. MeOH and 40 ml. ether to give 24.5 gms., m.p. 220°–8°.

| 2-[2-(1-[Methoxyphenyl]4-piperazinyl) ethylamino] benzamide | |
|---|---|
| Step 3: | 1-(p-Methoxyphenyl)-4-(2-chloroethyl) piperazine dihydrochloride | 24 gms. |
| | o-Aminobenzamide | 10 gms. |
| | Triethylamine | 30.7 ml. |
| | Diglyme | 250 ml. |

All starting materials were combined and heated at 150° for 96 hours. The reaction mixture was cooled, filtered, and the filtrate concentrated on the rotovap. The residue was triturated with 200 ml. isopropanol, filtered, and the solid recrystallized from 300 ml. 80% ethanol and then from a mixture of 60 ml. dimethylformamide and 100 ml. water to give 7.8 gms., m.p. 170°–2°

EXAMPLE VIII

Preparation of 1-[2-(1-Phenyl-4-piperazinyl ethyl]-2-phenyl-1,2,3,4-tetrahydro-4-quinazolinone hydrochloride

| 1-[2-(1-Phenyl-4-piperazinyl ethyl-2-phenyl-1,2,3,4-tetrahydro-4-quinazolinone | 10 gms. |
|---|---|
| Ethanol 95% | 100 ml. |

The base was dissolved in ethanol and 10 ml. of 2.5N HCl was added. After several hours the solid was filtered, washed with ethanol, and dried over P₂O₅ to give 100% yield of the HCl salt, m.p. 267°–71° (dec.).

EXAMPLE IX

Preparation of 1-[2-(1-Phenyl-4-piperazinyl) ethyl]-2-methyl-1,2,3,4-tetrahydro-4-quinazolinone hydrochloride

| 2-[2-(4-[1-Phenyl] piperazinyl) ethylamino] benzamide | 32.4 gms. |
|---|---|
| Acetic acid, glacial | 200 ml. |
| 1,1-Dimethoxyethane | 12.2 ml. |

The benzamide was dissolved in acetic acid, dimethoxyethane added and 3.5 ml. concentrated sulfuric acid added dropwise. The reaction mixture was stirred 5 hours, left overnight at room temperature, concentrated on the rotovap, and 75 ml. water added to the residue. The solution was made alkaline with 10% NaOH and extracted with benzene. The benzene extract was washed with water, dried, and concentrated to dryness. The benzene residue was dissolved in 90 ml. benzene and 100 ml. hexane was added to give 32 gms. crystalline material. This was suspended in 50 ml. 95% ethanol, 25 ml. 2.5N HCl added and heated to solution. A few more ml. 2.5N HCl was added, the solution treated with charcoal and cooled to give 30.5 gms. of the HCl salt. This was recrystallized twice from a 84% ethanol — 16% water mixture to give 18.5 gms., m.p. 242°–8° (2.05% water of hydration).

EXAMPLE X

Preparation of 1′-[2-(1-Phenyl-4-piperazinyl) ethyl]-1-methylspiro-[piperidine-4,2′(1′H) quinazolin]-4′(3′H)-one sulfate

| 2-[2-(4-[1-Phenyl] piperazinyl) ethylamino] benzamide | 19.4 gms. |
|---|---|
| Acetic acid, glacial | 120 ml. |
| 1-Methyl-4-piperidone | 12 ml. |

The benzamide was dissolved in acetic acid, 1-methyl-4-piperidone added and then 1.3 ml. sulfuric acid added dropwise. The reaction mixture was stirred 3 hours at room temperature, left over the weekend at room temperature, and heated 5 hours at 90°. 1-Methyl-4-piperidone (2 ml.) was added, the reaction mixture heated 7 hours at 90°, left overnight at room temperature and concentrated on the rotovap. The residue was dissolved in 150 ml. water. After several hours the solid was filtered off. The crude product was recrystallized twice from water and dried over P₂O₅ to give 11 gms. product, m.p. indefinite (starts at 160°), which contained 5% water of crystallization.

EXAMPLE XI

1-[2-(4-Hydroxy-4-phenylpiperidino)ethyl]-2-phenyl-1,2,3,4-tetrahydro-4-quinazolinone Methanesulfonate (776-278).

A mixture of 2-[2-(4-hydroxy-4-phenylpiperidino)ethylamino]benzamide (8 g), benzaldehyde (2.5 ml), piperidine (1.2 ml), and absolute ethanol (64 ml) was refluxed for 30 hrs. The solvent was removed on a rotovap. The thick oil was redissolved in 80 ml absolute ethanol and the solution treated with methanesulfonic acid. Ether (80 ml) was added and after 1 hr the product was filtered. The product was recrystallized from 71.5% ethanol; yield 8.5 g, m.p. 252°–254° C.

| | C | H | N | S |
|---|---|---|---|---|
| Calcd. | 64.03 | 6.33 | 7.85 | 6.12 |
| Found | 64.22 | 6.35 | 8.02 | 6.32 |

EXAMPLE XII

1-[2-(4-Propionoxy-4-phenylpiperidino)ethyl]-2-methyl-1,2,3,4-tetrahydro-4-quinazolinone (815-008)

To a solution of 11.85 g (0.03 mole) of 2-[2-(4-propionoxy-4-phenylpiperidino)ethylamio]benzamide in 70 ml DMF, made acid with approx. 3 ml conc HCl, was added 3.5 ml (0.033 mole) of 1,1-dimethoxyethane. The reaction mixture was stirred at room temperature for 5 hrs. The mixture was then poured into 800 ml H₂O and the solution made basic with a saturated solution of Na₂CO₃. After 1½ hrs the product was filtered and air dried. Recrystallization from MeOH yielded 9.5 (75%) of the product solvated with 3.8% MeOH, m.p. 116°–120°. Treatment with HCl yielded a mixture of mono- and di- hydrochlorides, m.p. 144°–147° (dec).

EXAMPLE XIII

1-[2-(4-Propionoxy-4-phenylpiperidino)ethyl]-2-phenyl-1,2,3,4-tetrahydro-4-quinazolinone Sulfate Dihydrate (776-284).

A mixture of 2-[2-(4-propionoxy-4-phenylpiperidino)ethylamino]benzamide (12.55 g), benzaldehyde (3.55 g), piperidine (1.35 g), and absolute ethanol (80 ml) was refluxed for 30 hrs. The solvent was removed on a rotovap. The thick oily product was chromatographed using silica gel and 5% isopropanol in chloroform. The product was isolated and dissolved in 30 ml 95% ethanol The solution was made acid with 4N $H_2SO_4$ and then 90 ml $H_2O$ was added. After 1 hr, the product was isolated and recrystallized from 850 ml 95% ethanol; yield 8.7 g, m.p. 186°–189°(d).

|  | C | H | N | S |
|---|---|---|---|---|
| Calcd | 65.44 | 6.59 | 7.63 | 2.91 |
| Found | 65.59 | 6.29 | 7.92 | 3.00 |

EXAMPLE XIV

1-[2-(4-Propionoxy-4phenylpiperidino)ethyl]-1,2,3,4-tetrahydro-4-quinazolinone (315-015)

2-(2-[4-Propionoxyoy-4-phenylpiperidino]ethylamino)benzamide was reacted with dimethoxymethane following the procedure described for 815-008. The mixture was heated at 70° for 15 hrs, adding additional conc HCl and dimethoxymethane to complete the reaction. Yield 50%, m.p. 141°–144°; hydrochloride melted at 187°–190°.

EXAMPLE XV

1-[2-(4-Propionoxy-4-phenylpiperidino)ethyl]-2,2-dimethyl-1,2,3,4-tetrahydro--b 4-quinazolinone (815-025)

To 11.85 g of 2-[2-(4-propionoxy-4-phenylpiperidino)ethylamino]-benzamide in 70 ml gl HOAc was added 1.5 ml conc $H_2SO_4$ and 2.7 ml acetone. The reaction mixture was stirred at room temperature for 48 hrs, added another 2 ml acetone and continued stirring for another 48 hrs. Three volumes of chloroform were added and the mixture basified with a saturated solution of $Na_2CO_3$. The choloroform fraction yielded 84% of the product after recrystallization from MeOH, m.p. 167°–169°; hydrochloride melted at 210° (dec).

EXAMPLE XVI

1-[2-(4-Propionoxy-4-phenylpiperidino)ethyl]-2-phenyl-3-methyl-1,2,3,4-tetrahydro-4-quinazolinone Maleate (815-059)

Step 1-
N-Methyl-2-(2-[4-propionoxy-4 phenylpiperidino]ethylamino)-benzamide (815-048)

This compound was prepared by following substantially the same procedure described for 776-262 but substituting 2-amino-N-methylbenzamide for 2-aminobenzamide in Step 1.

Step 2-
1-[2-(4-Propionoxy-4-phenylpiperidino)ethyl]-2-phenyl-3-methyl 1,2,3,4-tetrahydro-4-quinazolinone Maleate N-Methyl-2-(2-[4-propionoxy-4-phenylpiperidino]ethylamino)benzamide was reacted with benzaldehyde following the procedure described for 815-008. The mixture was heated at 70° for 13 hours to complete the reaction. The crude product was chromatographed using silica gel and 2% isopropanol in chloroform: yield of the maleate salt was 53%, m.p. 168°–170°.

EXAMPLE XVII

Preparation of 1-[2-(1-Phenyl-4-piperazinyl)ethyl]-2-(p-acetamidophenyl)-1,2,3,4-tetrahydro-4-quinazolinone (753-465)

2-[2-(4-[1-Phenyl] piperazinyl) ethyl-amino] benzamide (24.3g.) 3.6 g. piperidine, 12.6g. p-acetamidobenzaldehyde, and 225 ml. anhydrous ethanol were refluxed with stirring for 26–28 hours, cooled, and concentrated to dryness. The residue was triturated with cold water and filtered, washed with water, and dried to give a yellow solid. This was recrystallized from benzene to give 24.6g. solid. The solid was recrystallized from 1600 ml. ethyl acetate to give 10.6 g. This was combinded with 10.2 g. recovered from the ethyl acetate mother liquor and the total solid disolved in 2700 ml. ethyl acetate and concentrated to 300 ml. The solid was filtered, washed with ethyl acetate and dried to give 22.6g. (about 10% solvent). A 7.6g. portion of the product was dried over $P_2O_5$, under high vacuum at 105° overnight, then for 8 hours at 115° give 6.3g, m. 182°-5°.

|  | C | H | N |
|---|---|---|---|
| Calcd. | 71.61 | 6.65 | 14,92 |
| Found | 71.40 | 6.70 | 14.88 |

PHARMACOLOGICAL ACTIVITY OF COMPOUNDS OF THIS INVENTION

The compounds of this invention, when administered to several species of experimental animals by various routes, have found to posses effective analgesic activity and can antagonize strong narcotic analgesics as indicated by use of conventional testing methods. These compounds are characterized further by a very low order of toxicity in experimental animals and appear to be substantially non-addicting. In addition to the primary analgesic activity these compounds possess other pharmacological effects of potential utility at higher dose levels than those required for analgesia, but within an adequeate margin of safety for consideration of therapeutic application. Among these other pharmacological properties are tranquilizing activity, hypothermic activity, anticonvulsant activity, antihistaminic activity, and In some cases, suspensions of the test compound as the base were used, and in others, solutions and suspensions of the hydrochloride salt were used in testing for analgesia and other pharmacological properties. Different lots of the compounds prepared as disclosed have not been found to display significant differences.

Analgesics

Established methods were employed for demonstrating analgesia and consisted of the following: A modification of the Eddy and Leimbach (Exp. Biol. & Med. 95:729, (1957)) mouse hot plate test was used. The end point of this test is the time required for animals, pretreated with various dose levels of the test compounds or standard analgesics such as morphine or codeine, to react to the heat stimulus by raising or licking the feet or by jumping. The dose of compound or standard which results in significant analgesic effect in 50% of the animals is calculated on the basis of the number showing response times exceeding the means control time by 2 seconds or more. Ten animals are used for each dose level.

In addition to the hot plate method, the writhing test described by Sigmund et al., Soc. Exp. Biol. and Med. 95:729 (1975) has been applied in both rats and mice as further indication of analgesics. This method has been reported to be of value in detecting activity of narcotic antagonist analgesics which sometimes do not exhibit activity with use of other conventional methods. The stimulus of intraperitoneal injection of phenylbenzoquinone results in a writhing syndrome characterized by periodic twisting and stretching of the body with extension of the hind legs. Frequency of writhing has been shown to be reduced or prevented by prior administration of narcotic and non-narcotic analgesics. A test compound is considered to have analgesic properties if, by prior administration, it is able to reduce significantly the number of writhes from that obtained by a group receiving vehicle alone. The dose of compound protecting 50% of the animals is determined and expressed as the $ED_{50}$. Ten animals are used at each dose level.

Narcotic Antagonists

Certain compounds have the ability to antagonize the activity of strong narcotic analgesics in animals, whereas when tested by conventional methods in mice and rats little or no analgesia can be demonstrated. Some of these compounds have been shown to be very effective analgesics in man. The compounds of this invention were tested for their ability to antagonize narcotic analgesics by two different tests. When oxymorphone, a morphine derivative, is administered to mice, pupil dilation occurs. It has been demonstrated in our laboratory that narcotic antagonists are able to reduce this mydriatic response significantly if administered prior to oxymorphone whereas narcotic agents such as morphine and codeine cause no change or an increase in the pupil size. Another test used for narcotic antagonist activity was published by Harris & Pearson. This test is modification of the D'Amour & Smith method.

In the original method the time required for rats to flick their tails following application of a heat stimulus is taken as a measure of analgesic potency. As modified by Harris & Pearson the drug being tested for narcotic antagonism is administered prior to the morphine. An antagonist reduces or prevents analgesia from the morphine. both of the methods described have been utilized to test the narcotic antagonist characteristics of the compounds of the examples.

Local Anesthetic Activity

An effective local anesthetic causes a blockade of the nerves of the lower leg and foot causing the animal, when permitted to walk, to do so flatfooted, rather than its normal habit, up on its toes. Alternatively an effective local anesthetic, by the sciatic block method, can cause the leg to be dragged by the animal when walking so long as effective sciatic block persits. Toxic agents may effect the same apparent results, but the blockade effected by toxic agents is irreversible. However, in contrast to toxic agents, an effective local anesthetic permits recovery of the use of the leg and foot after a period of time.

The mice used in the sciatic block test were placed in a holder with their hind limbs extended. A quantity of the test compound (e.g. 0.05 ml) was injected into the area surrounding the sciatic nerve at the juncture of the two major leg muscles. Effective local anesthetic activity is indicated in Table IV ("Pos." —meaning that the blockade did take place and that the leg and foot returned to normal after a time.)

Analgesic Activity

Results:

Tables I and IV summarize the results obtained with the compounds of this invention when tested for analgesic acitivity and provides a comparison with morphine and codeine.

For example, compound 740-222 (the compound of Example II) is more active by the oral than the parenteral route, an unusual characteristic. Analgesic activity of this compound is of the same order as codeine and slightly less than morphine by the oral route utilizing the hot plate test in mice. By the writing test in mice this compound has approximately one third the activity of morphine and is about 1½ times as active as codeine. The writhing syndrome is also 50% blocked in rats pretreated with 10 mg/Kg of 740-222 by the oral route. The compound produces a slight antagonism of oxymorphone induced mydriasis in mice by the intraperiteneal route only. It was not effective by the subcutaneous route in antagonizing morphine analgesia in rats. This may have been due to its low solubility, causing a poor absorption by this route.

The acute toxicity of compound 740-222 by all routes tested in mice is greater than 1 gm/kg body weight which is substantially above effective analgesic doses. The therapeutic index i.e. the relationship of the lethal dose to the effective dose for this compound by the oral route is greater than 300. The highest dose that can be administered without gross evidence of sedation is approximately 10 times that necessary to produce effective analgesia.

Table I also indicates the results of testing compound 730-372 (the compound of Example I) for analgesic activity. This compound is more active by the parenteral routes than by the oral route. By the hot plate and writhing tests 730-372 has been found to be approximately equivalent to or slightly more active than morphine. It was effective in antagonizing oxymorphone induced mydriasis and at lower dose levels antagonism of morphine analgesia was observed in rats. These data support the contention that this compound is a narcotic antagonist analgesic.

TABLE I

Analgesic Activity of 740-222 & 730-372

| Compound | Species | Route | Hot Plate $ED_{50}$ | Writhing $ED_{50}$ | HNSD./$ED_{50}$ H.P. | HNSD./$ED_{50}$ Writhing | $LD_{50}/ED_{50}$ H.P. | $LD_{50}/ED_{50}$ Writhing |
|---|---|---|---|---|---|---|---|---|
| 740-222 | Mouse | p.o. | 20 | 11 | 5 | 9 | >50 | >91 |
| | Mouse | i.p. | 52 | — | 3.4 | — | >17 | — |
| | Mouse | s.c. | >562 | — | — | — | — | — |
| | Rat | p.o. | | ≈ 14 | | 7.1 | | 71 |
| | D'Amour Smith | Rat Tail Flick p.o. $ED_{50}$ | | >100 mg/kg | | | | |
| 730-372 | Mouse | p.o. | 3.0 | 2.9 | 1.9 | 1.9 | >330 | >340 |
| | Mouse | i.p. | 1.5 | | 1.2 | — | 670 | — |
| | Mouse | s.c. | 4.1 | 1.6 | 2.4 | 6.3 | >240 | >620 |
| | Rat | Sub. cut | | 2.5 | | 2.0 | | 400 |
| | D'Amour Smith | Rat Tail Flick Sub. cut. ED/$_{50}$ | | >18 mg/kg | | | | |
| Morphine | Mouse | p.o. | 14 | 3 | 4.0 | 19.0 | 570 | 267 |
| | Mouse | i.p. | 2.5 | — | 4.0 | — | 100 | — |
| | | Rat Tail Flick Sub. cut. $ED_{50}$ | | 15 mg/kg | | | | |
| Codeine | Mouse | p.o. | 20 | 17 | 5.0 | 5.9 | 27 | 32 |
| | Mouse | i.p | 12 | — | 2.6 | — | 8.7 | — |

HNSD=highest dose which can be administered without development of any gross symptoms such as depression, convulsions etc.

The acute toxicity of compound 730-372 (as indicated by the $LD_{50}$) is shown in Table II to be greater than 800 to 1000 mg/kg body weight when assessed in mice by various routes of administration. The therapeutic index is greater than 300.

TABLE II

ACUTE TOXICITIES

| Species | Route of Administration | 740-222 $LD_{50}$ (48 hr) mg/kg | 730-372A $LD_{50}$ (48 hr) mg/kg | Morphine $LD_{50}$ (48 hr) | Codeine $LD_{50}$ (48 hr) |
|---|---|---|---|---|---|
| Mouse | p.o. | >10,000 | >1000 | ≈ 800 | 540 |
| | i.p. | > 2,500 | >1000 | 250 | 104 |
| | i.v. | — | 50 | | |
| | s.c. | > 1,000 | >1000 | — | — |

NOTE: Compounds were administered in 2% clearjel as a suspension except in the case of i.v. 730-372A which was a solution (5mg/ml) in distilled water. Exact $LD_{50}$ values could not be obtained due to low compound solubility limiting the concentration which could be administered.

| | | | | | |
|---|---|---|---|---|---|
| Rat | p.o. | — | — | | |
| | s.c. | >1,000* | >1000* | | |
| | i.p. | — | — | | |
| Cat | p.o. | >1,000* | | | |
| | i.p. | >1,000* | >1000* | | |

*=preliminary result
Toxicities have only been run with male animals to date.
Studies using females will begin shortly.

Tranquilizer Activity

A tranquil sedation has been observed in mice, cats and monkeys following administration of these compounds in doses exceeding those that are required for analgesia. In addition further indirect evidence for tranquilizer activity has been obtained by application of a method described by Witkin et al., J. Pharmacol, and Exp. Ther. 126:330 (1959)

This test is based upon observations that the pinna reflex of the mouse is blocked at relatively low doses of major tranquilizer drugs whereas very high doses are needed to block the corneal reflex. A ratio of $ED_{50}$ corneal/$ED_{50}$ pinna exceeding unity is taken as evidence of tranquilizer type action. The compound 740-222 (the compound of Example II) displayed a ratio of greater than 10 and is therefore classified as possessing tranquilizer activity. Preliminary results with compound 730-372 (the compound of Example I) indicate a ratio of approximately 0.5 which is within the range of ratios expected with sedatives (0.3 to 0.7) and approaches the range of ratios for minor tranquilizers with central muscle relaxant activity.

These compounds have been tested for antihistaminic properties utilizing segments of isolated guinea pig ileum suspended in Kreg Ringer solution maintained at 37° C. with aeration of a 95% $O_2$ + 5% $CO_2$ mixture. Contractions were elicited by histamine phosphate. The concentration of compound required to block these contractions when added to the tissue bath prior to introduction of histamine is taken as evidence for antihistaminic action. Table III reveals that 740-222 has about the same activity as the standard antihistaminic diphenhydramine and compound 730-372 is about half as active as the standard.

Hypothermic Effect

Rectal temperatures were recorded periodically in mice following administration of 740-222 by oral route. Codeine was used for comparison. This compound effectively reduced body temperature in normal mice. Compound 730-372 was also effective in this respect.

Anticonvulsant Activity

Administration of pentylentetrazol (Metrazol) to mice resulted in convulsive seizures which could be blocked or reduced effectively by anticonvulsant agents, such as phenobarbital. Compound 740-222 administered by the oral route was able to antagonize these metrazol induced convulsions in mice. Comopund 730-372 was not effective by the subcutaneous route in this respect.

Gastrointestinal Motility Suppression

The opium alkaloids are the most effective agents for causing constipation or treating diarrhea. It has been found that 720-222 is effective in suppressing intestinal motility in mice. The method used was a modification of that described by Brittain & Collier (J. Phsiol. 141:14p, (1958). In this method the length of intestine traversed by an orally administered suspension of charcoal is measured. Compounds which inhibit motility effectively, reduce the percentage of the small intestine traversed. 740-222 reduces gut motility as indicated by a comparison with codeine. This effect is less important with compound 730-372.

Unless otherwise indicated, the test compounds of Table IV are the title compounds of the Examples hereof to which reference is made in Table IV.

TABLE III

Activity of 740-222 and 730-372 on isolated guinea pig ileum screen

| Compound | Amount in micrograms to produce a 50% block of: | |
|---|---|---|
| | Acetylcholine | Histamine |
| 740-222 | 1000 | 0.5 |
| 730-372 | 126 | 0.8 |
| Diphenhydramine | 6 | 0.4 |

TABLE IV

| | TOXICITY | | ANALGESIA | | MOUSE TAIL STIMULATION ED$_{50}$ | LOCAL ANESTHESIA | NARCOTIC |
|---|---|---|---|---|---|---|---|
| | | | PHENYLBENZO-QUINONE WRITHING ED$_{50}$ | | | | |
| EXAMPLE | HNSD$^1$ I.P. | LD$_{50}^2$ I.P.$^4$ | P.O.$^3$ mg/kg | S.C.$^5$ mg/kg | S.C. mg/kg | SCIATIC BLOCK | ANTAGONISM I.P. |
| XI* | 30 | 300 | 100 | 100 | 30 | — | Negative |
| XII (Base) | 0.3 | 10 | 1.5 | 0.005 | — | — | Negative |
| XII (HCl) | 0.1 | 150 | 24.5 | 0.1 | — | — | Negative |
| XIII | 0.001 | 0.3 | 0.18 | 0.016 | — | Insol | Negative |
| XIV (Base) | 0.1 | 200 | 15 | 0.027 | — | — | Negative |
| XIV (HCl) | 0.1 | 200 | 7.6 | 0.021 | — | — | Negative |
| XV (Base) | 0.1 | 200 | 0.98 | 0.0012 | — | — | Negative |
| XV (HCl) | 0.03 | 150 | 2.8 | 0.0015 | — | — | Negative |
| XVI | 0.001 | 10 | 0.83 | 0.00011 | — | — | Negative |
| XVII | 10 | 30 | 5 | 60 | — | Negative | Positive |
| Controls: | | | | | | | |
| Morphine | 10 | 380 | 2.6 | 0.5 | 1.5 | Negative | Negative |
| Meperidine | 30 | 130 | 18.0 | 1.7 | 1.8 | Positive | Negative |
| Pentazocine | 30 | 140 | 56 | 2.0 | — | Positive | Positive |
| 1-[2-(4-phenylpiperidino)ethyl]-2-phenyl-1,2,3,4-tetrahydro-4-quinazolinone | 10 | 100 | 20 | 2 | — | — | Positive |

$^1$HNSD : Highest Nonsymptomatic Dose
$^2$LD$_{50}$ : Median Lethal Dose
$^3$P.O. : Oral
$^4$I.P. : Intraperitoneal
$^5$S.C. : Subcutaneous
* : may be used as intermediate for XIII

What is claimed is:

1. A member of the group consisting of (a) a compound of the formula:

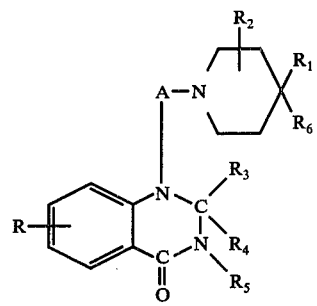

wherein
R is H, lower alkyl, hydroxy, lower alkoxy, halogen, amino, nitro, —NHCHO or —NHCOCH$_3$;
A is (CH$_2$)$_n$, where $n$ is 1–5, or branched chain alkylene of 3–5 carbons;
R$_1$ is phenyl;
R$_2$ is H or lower alkyl;
R$_3$ and R$_4$ are separately selected from H, lower alkyl, phenyl, phenyl substituted in the ring with OH, NH$_2$, OCH$_3$, Cl or —NHCOCH$_3$, phenyl lower alkyl-, and phenyl lower alkyl- substituted in the ring with OH, NH$_2$, OCH$_3$ or Cl; or R$_3$ and R$_4$ join together with the 2-position carbon atom to which they are attached to form a methylene ring having 3–10 carbons;
R$_5$ is H, lower alkyl, phenyl, phenyl lower alkyl-, or phenyl substituted in the ring with OH, NH$_2$, OCH$_3$, Cl or —NHCOCH$_3$;
R$_6$ is propionazy;
and (b) a pharmacologically acceptable acid addition salt thereof.

2. A member of the group consisting of (a) compound of the formula:

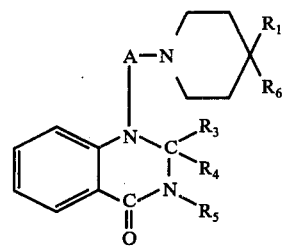

wherein:
A is (CH$_2$)$_2$;
R$_1$ is phenyl;
R$_3$ and R$_4$ are separately selected from H, lower alkyl, phenyl, phenyl substituted in the ring with OH, NH$_2$, OCH$_3$, Cl or —NHCOCH$_3$, phenyl lower alkyl-, and phenyl lower alkyl-substituted in the ring with Oh, NH$_2$, OCH$_3$or Cl; or R$_3$ and R$_4$ join together with the 2-position carbon atom to which they are attached to form a methylene ring having 3–10 carbons;

$R_5$ is H, lower alkyl, phenyl, phenyl lower alkyl-, or phenyl substituted in the ring with OH, $NH_2$, $OCH_3$, Cl or $-NHCOCH_3$;

$R_6$ is propionoxy;

and (b) a pharmacologically acceptable acid addition salt thereof.

3. The compound of claim 2, wherein $R_3$ is phenyl and each of $R_4$ and $R_5$ is hydrogen.

4. The compound of claim 2 wherein $R_5$ is hydrogen and each of $R_3$ and $R_4$ is methyl.

5. The compound of claim 2 wherein $R_3$ is phenyl, $R_4$ is hydrogen and $R_5$ is methyl.

* * * * *